US008642746B2

(12) United States Patent
Phillips et al.

(10) Patent No.: US 8,642,746 B2
(45) Date of Patent: Feb. 4, 2014

(54) UNIQUE CALIBRATOR POLYNUCLEOTIDES AND METHODS OF USING IN QUANTITATIVE NUCLEIC ACID ASSAYS

(75) Inventors: Christopher S. Phillips, Forest Hill, MD (US); Albert L. Ruff, Abingdon, MD (US); James F. Dillman, III, Abingdon, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 747 days.

(21) Appl. No.: 12/667,273

(22) PCT Filed: Jul. 10, 2008

(86) PCT No.: PCT/US2008/069632
§ 371 (c)(1),
(2), (4) Date: Dec. 30, 2009

(87) PCT Pub. No.: WO2009/012110
PCT Pub. Date: Jan. 22, 2009

(65) Prior Publication Data
US 2010/0330562 A1    Dec. 30, 2010

Related U.S. Application Data

(60) Provisional application No. 60/949,677, filed on Jul. 13, 2007.

(51) Int. Cl.
*C07H 21/04* (2006.01)

(52) U.S. Cl.
USPC ........................................ 536/23.1; 536/24.3

(58) Field of Classification Search
None
See application file for complete search history.

(56) References Cited

U.S. PATENT DOCUMENTS

| | | |
|---|---|---|
| 6,312,929 B1 | 11/2001 | McMillan |
| 6,691,041 B2 | 2/2004 | Sagner |
| 7,118,867 B2 | 10/2006 | Tabiti |
| 2002/0058262 A1 | 5/2002 | Sagner |
| 2005/0095603 A1 | 5/2005 | Mokkapati |
| 2005/0239116 A1 | 10/2005 | Willey |

FOREIGN PATENT DOCUMENTS

WO    01/46463 A2    6/2001

OTHER PUBLICATIONS

Boonham et al. Journal of Virological Methods 116(2004) 139-146.*
Boonham et al. (Journal of Virological Methods 116(2004)139-146).*
GenBank Accession U23058; obtained from http://www.ncbi.nlm.nih.gov/nuccore/U23058.1?report=GenBank[Jun. 22, 2012 1:36:25 PM], five pages.*
Celi et al. Nucleic Acids Research, 1993, vol. 21, No. 4, p. 1047.*
Gora-Sochacka et al. RNA. 1997. 3:68-74.*
Gruner. Virology 209, 60-69, 1995.*
GenBank AY372398.1, Potato spindle tuber viroid isolate 21008470, complete genome, Jan. 6, 2006, two pages.*
Verhoeven et al. (Eur. J. Plant Pathol. 110, 823-831.*
International Preliminary Report on Patentability for PCT/US2008/069632 mailed Jan. 19, 2010.
International Search Report and Written Opinion for PCT/US2008/069632 mailed Jan. 30, 2009.
Verhoeven, J. et al. (2004) "Natural Infections of Tomato by Citrus exocortis viroid, Columnea latent viroid, Potato spindle tuber viroid and Tomato chlorotic dwarf viroid" European Journal of Plant Pathology 110:823-831.
Ozbek, A. et al. (2003) "Evaluation of Two Recovery Methods for Detection of *Mycobacterium avium* subsp. paratuberculosis by PCR: Direct-dilution-centrifugation and C18-carboxypropylbetaine Processing" FEMS Microbiology Letters 229:145-151.
Rensen, G. et al. (2006) "Development and Evaluation of a Real-Time FRET Probe Based Multiplex PCR assay for the Detection of Prohibited Meat and Bone Meal in Cattle Feed and Feed Ingredients" 3(4):337-347.
European Search Report received in EP 08781603, mailed Aug. 10, 2011.
S. A. Bustin, 'Quantification of mRNA using real-time reverse transcription PCR (RT-PCR): trends and problems', Journal of Molecular Endocrinology, 2002, vol. 29, pp. 23-39.
S. A. Bustin, et al., 'Quantitative real-time RT-PCR—a perspective', Journal of Molecular Endocrinology, 2005, vol. 34, pp. 597-601.
H. Bostan, et al., 'An RT-PCR primer pair for the detection of Pospiviroid and its application in surveying ornamental plants for viroids', Journal of Virological Methods, 2004, vol. 116, pp. 189-193.

\* cited by examiner

*Primary Examiner* — Juliet Switzer
(74) *Attorney, Agent, or Firm* — Elizabeth Arwine

(57) ABSTRACT

Disclosed herein are polynucleotides which may be used to calibrate or standardize quantitative nucleic acid assays. As disclosed, the polynucleotides comprise a sequence derived from a plant viroid polynucleotide or a bacterial or chloroplast Type II intron polynucleotide. Also disclosed are methods of making and using the polynucleotides.

6 Claims, 4 Drawing Sheets

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: PVS target sequence

<400> SEQUENCE: 1
ctgtcgcttc ggctactacc cggtg                                       25

<210> SEQ ID NO 2
<211> LENGTH: 30
<212> TYPE: DNA
<213> ORGANISM: Artificial Sequence
<220> FEATURE:
<223> OTHER INFORMATION: CLS target sequence

<400> SEQUENCE: 2
agatgcgttc cgctttacaa ctaacgaaca                                  30

<210> SEQ ID NO 3
<211> LENGTH: 80
<212> TYPE: DNA
<213> ORGANISM: Artificial Sequence
<220> FEATURE:
<223> OTHER INFORMATION: Example of calibrator polynucleotide

<400> SEQUENCE: 3
ggagtaattc ccgccgaaac agggttttcc tgtcgcttcg gctactaccc ggtggaaaca    60
actgaagctc ccgagaaccg                                                80
```

```
<210> SEQ ID NO 4
<211> LENGTH: 95
<212> TYPE: DNA
<213> ORGANISM: Artificial Sequence
<220> FEATURE:
<223> OTHER INFORMATION: Example of calibrator polynucleotide

<400> SEQUENCE: 4
gaactcccgg aattgatgga attatctggt agatgcgttc cgctttacaa ctaacgaaca      60
agggctacaa gtacattcga aagaagaacg gtaaa                                 95

<210> SEQ ID NO 5
<211> LENGTH: 141
<212> TYPE: DNA
<213> ORGANISM: Artificial Sequence
<220> FEATURE:
<223> OTHER INFORMATION: Example of calibrator polynucleotide
<220> FEATURE:
<221> NAME/KEY: misc_feature
<222> LOCATION: (41)..(41)
<223> OTHER INFORMATION: n is a, c, g, or t

<400> SEQUENCE: 5
ggagtaattc ccgccgaaac agggttttca cccttccttt nttcgggtgt ccttcctcgc      60
gcccgcagga ccacccctcg cccctttgcg ctgtcgcttc ggctactacc cggtggaaac     120
aactgaagct cccgagaacc g                                               141

<210> SEQ ID NO 6
<211> LENGTH: 131
<212> TYPE: DNA
<213> ORGANISM: Artificial Sequence
<220> FEATURE:
<223> OTHER INFORMATION: Example of calibrator polynucleotide

<400> SEQUENCE: 6
gaactcccgg aattgatgga attatctggt catcgtcggc agataagatg cgttccgctt      60
tacaactaac gaacaagggc taccgtgcaa aaccattaac acgaaagtac attcgaaaga     120
agaacggtaa a                                                          131

<210> SEQ ID NO 7
<211> LENGTH: 358
<212> TYPE: DNA
<213> ORGANISM: Artificial Sequence
<220> FEATURE:
<223> OTHER INFORMATION: Example of calibrator polynucleotide
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 7
cggaactaaa ctcgtggttc ctgtggttca cacctgacct cctgagcaga aaagaaaaaa      60
gaattgcggc tcggaggagc gcttcagggc atcccggggg aaacctggag cnaactggca     120
ataaggcggt gggaagtggc caacggncga caggagtaat tcccgccgaa acagggtttt     180
cacccttcct ttnttcgggt gtccttcctc gcgcccgcag gaccacccct cgcccctttg     240
cgctgtcgct tcggctacta cccggtggaa acaactgaag ctcccgagaa ccgcttttc     300
```

```
tctatcttcc ttgcttcggg gcgagggtgt ttagcccttg aaccgcagt tggttcct        358
```

<210> SEQ ID NO 8
<211> LENGTH: 623
<212> TYPE: DNA
<213> ORGANISM: Artificial Sequence
<220> FEATURE:
<223> OTHER INFORMATION: Example of calibrator polynucleotide

<400> SEQUENCE: 8

```
aagcattgat tggaaaagag ttaaagaagt tgttaataac cttcagtctc gaattgcaag        60
tgcagctaag aacggaaaat ggataaccgt gaacaaactc tcccgtcttc tgacccggtc       120
cttatatgcc aaactacttt cagttcgtaa agtaaccact aacaagggaa gccgaactcc       180
cggaattgat ggaattatct ggtcatcgtc ggcagataag atgcgttccg ctttacaact       240
aacgaacaag ggctaccgtg caaaaccatt aacacgaaag tacattcgaa agaagaacgg       300
taaactacga cctcttagca taccaactat gtatgacaga gcaatgcaaa ccctgcactc       360
tctggtgcta ggtccaatcg aatctgctat aggtgacaag acttcgtttg ggtttaaacc       420
ttaccgctca actaaagatg cttacgccta ccttcacatc tgtttaagca agaaaattgc       480
tcctgaatgg attgtcgaag gtgatattaa agcctgcttt gatgaaatca accacacttg       540
gatacttgac aacatcccta tggataaacg aatccttaag gagtttctaa aagccggata       600
tgtcgagaat tatcatctgt ttc                                              623
```

<210> SEQ ID NO 9
<211> LENGTH: 33
<212> TYPE: DNA
<213> ORGANISM: Artificial Sequence
<220> FEATURE:
<223> OTHER INFORMATION: Forward primer used to amplify SEQ ID NO:3

<400> SEQUENCE: 9

```
cgtagcggta ccggagtaat tcccgccgaa aca                                    33
```

<210> SEQ ID NO 10
<211> LENGTH: 33
<212> TYPE: DNA
<213> ORGANISM: Artificial Sequence
<220> FEATURE:
<223> OTHER INFORMATION: Reverse primer used to amplify SEQ ID NO:3

<400> SEQUENCE: 10

```
cgccgggtcg accggttctc gggagcttca gtt                                    33
```

<210> SEQ ID NO 11
<211> LENGTH: 34
<212> TYPE: DNA
<213> ORGANISM: Artificial Sequence
<220> FEATURE:
<223> OTHER INFORMATION: Forward primer used to amplify SEQ ID NO:4

<400> SEQUENCE: 11

```
cgtagcggta ccgaactccc ggaattgatg gaat                                   34
```

<210> SEQ ID NO 12
<211> LENGTH: 40
<212> TYPE: DNA
<213> ORGANISM: Artificial Sequence
<220> FEATURE:
<223> OTHER INFORMATION: Reverse primer used to amplify SEQ ID NO:4

<400> SEQUENCE: 12

```
cgccgggtcg actttaccgt tcttctttcg aatgtacttg                          40

<210> SEQ ID NO 13
<211> LENGTH: 18
<212> TYPE: DNA
<213> ORGANISM: Artificial Sequence
<220> FEATURE:
<223> OTHER INFORMATION: Forward primer anneals to nucleotides 1-18 on
      the parent plasmid (pTNT from Promega, GenBank accession
      #AF479322)

<400> SEQUENCE: 13
taaggctaga gtacttaa                                                  18

<210> SEQ ID NO 14
<211> LENGTH: 18
<212> TYPE: DNA
<213> ORGANISM: Artificial Sequence
<220> FEATURE:
<223> OTHER INFORMATION: Reverse primer anneals to nucleotides 195-213
      on the parent plasmid (pTNT from Promega, GenBank accession
      #AF479322)

<400> SEQUENCE: 14
ggatccaaaa aacccctc                                                  18
```

US 8,642,746 B2

UNIQUE CALIBRATOR POLYNUCLEOTIDES AND METHODS OF USING IN QUANTITATIVE NUCLEIC ACID ASSAYS

This application is a 371 of PCT/US2008/069632, filed 10 Jul. 2008, and claims the benefit of U.S. Patent Application Ser. No. 60/949,677, filed 13 Jul. 2007, both of which are herein incorporated by reference in their entirety.

ACKNOWLEDGMENT OF GOVERNMENT SUPPORT

Employees of the United States Army made this invention. The government has rights in the invention.

BACKGROUND OF THE INVENTION

1. Field of the Invention

The present invention generally relates to calibrator nucleic acid molecules. The calibrator nucleic acid molecules may be used in qualitative and quantitative nucleic acid assays such as quantitative real-time PCR assays.

2. Description of the Related Art

Quantitative real-time polymerase chain reaction (Q-PCR) is used to accurately quantitate the level of messenger RNA (mRNA) for a polynucleotide of interest in a biological sample. Currently, Q-PCR is the most sensitive and robust technique for the quantitation of mRNA and the determination of expression levels of a gene. The quantitation of mRNA by Q-PCR is determined in relation to an internal reference gene that is expressed at constant levels in a series of samples. Several internal reference genes, such as beta-actin, GAPDH, and the like, have been used in Q-PCR and are referred to as "housekeeping" genes. That is, the expression level of these genes has been thought to remain relatively constant across a sample set.

Use of housekeeping genes, however, is not always appropriate since various experimental conditions have been shown to alter the levels of housekeeping genes. In these situations, a known amount of a calibrator polynucleotide that is added to the sample prior to processing and analysis may be used. The calibrator polynucleotide then becomes the internal reference standard for the Q-PCR assay. The levels of the calibrator polynucleotide are independent of the experimental conditions, thereby resulting in an accurate internal standard.

The theoretical utility of a calibrator polynucleotide has been discussed previously. Bustin described the use of universal controlled reference polynucleotides to control for reverse transcriptase and PCR efficiencies. See Bustin, S. A. (2002) Quantification of mRNA using real-time reverse transcription PCR (RT-PCR): trends and problems. J. Molecular Endocrinology. 29:23-39, which is herein incorporated by reference. Unfortunately, as explained by Bustin, externally added calibrator polynucleotides are not widely accepted and commercially available as validated universal calibrated polynucleotides which is reiterated by Huggett et al. See Huggett et al. (2005) Real-time RT-PCR normalization; strategies and considerations. Genes and Immunity. 6:279-284.

Thus, a need still exists for universal and validated calibrator polynucleotides for quantitative and qualitative nucleic acid assays such as quantitative real-time PCR assays.

SUMMARY OF THE INVENTION

The present invention generally relates to nucleic acid molecules that may be used to calibrate nucleic acid hybridization assays.

In some embodiments, the present invention provides an isolated nucleic acid molecule comprising at least 18 consecutive nucleotides of a plant viroid sequence, a bacterial type II intron, a chloroplast type II intron, or a complementary sequence thereof. In some embodiments, the nucleic acid molecule consists of 18 to about 620, preferably 18 to about 200, more preferably 18 to about 150, most preferably 18 to about 100, consecutive nucleotides of the plant viroid sequence, the bacterial type II intron, the chloroplast type II intron, or the complementary sequence thereof. In some embodiments, the plant viroid sequence is from a potato tuber viroid and the chloroplast type II intron is from *Methanosarcina acetivorans*. In some embodiments, the plant viroid sequence is SEQ ID NO:7 and the chloroplast type II intron is SEQ ID NO:8. In some embodiments, the isolated nucleic acid sequence is selected from the group consisting of SEQ ID NO:1 or its complement thereof; SEQ ID NO:2 or its complement thereof; SEQ ID NO:3 or its complement thereof; SEQ ID NO:4 or its complement thereof; SEQ ID NO:5 or its complement thereof; SEQ ID NO:6 or its complement thereof; SEQ ID NO:7 or its complement thereof; and SEQ ID NO:8 or its complement thereof. As used herein, when referring to the number of nucleotides in a sequence, "about" refers to ±1 to 5 nucleotides. Thus, "about 100" nucleotides refers to 95 to 105 nucleotides.

In some embodiments, the present invention provides a primer or a probe which specifically hybridizes to the isolated nucleic acid molecule according to the present invention. In some embodiments, the primer or probe comprises or consists of 18 to about 250, preferably 18 to about 200, more preferably 18 to about 150, most preferably 18 to about 100 nucleotides. In some embodiments, the sequence of the primer or probe is selected from the group consisting of SEQ ID NO:1 or its complement thereof; SEQ ID NO:2 or its complement thereof; SEQ ID NO:9 or its complement thereof; SEQ ID NO:10 or its complement thereof; SEQ ID NO:11 or its complement thereof; and SEQ ID NO:12 or its complement thereof.

In some embodiments, the present invention provides an isolated nucleic acid molecule which contains a primer or probe according to the present invention and at least one intervening polynucleotide. In some embodiments, the isolated nucleic acid molecule further comprises at least one flanking polynucleotide. In some embodiments, the isolated nucleic acid molecule consists of the primer or probe according to the present invention and at least one intervening polynucleotide and optionally at least one flanking polynucleotide.

In some embodiments, the present invention provides assays which comprise using an isolated nucleic acid molecule or a primer or probe according to the present invention as a primer, a probe, or a control.

In some embodiments, the present invention provides a method of determining the validity, sensitivity, specificity, or accuracy of a quantitative nucleic acid assay for a given nucleic acid molecule in a test sample which comprises adding at least one isolated nucleic acid molecule according to the present invention to the test sample; amplifying the given nucleic acid molecule; detecting or quantifying the amount of the given nucleic acid molecule and the amount of the isolated nucleic acid molecule; and using the amount of the isolated nucleic acid molecule as a control.

In some embodiments, the present invention provides a kit comprising an isolated nucleic acid molecule or a primer or probe according to the present invention packaged together with at least one reagent for conducting a nucleic acid hybridization assay.

In some embodiments, the nucleic acid molecule is 95% to 100%, preferably 96% to 100%, more preferably 97% to 100%, even more preferably 98% to 100%, most preferably 99% to 100%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a complement thereof.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 shows the construction of SEQ ID NO:2 and SEQ ID NO:3 and generation of templates for in vitro production. Specifically, the target sequences were amplified by PCR from ssDNA oligonucleotides.

DETAILED DESCRIPTION OF THE INVENTION

Figure 1A:
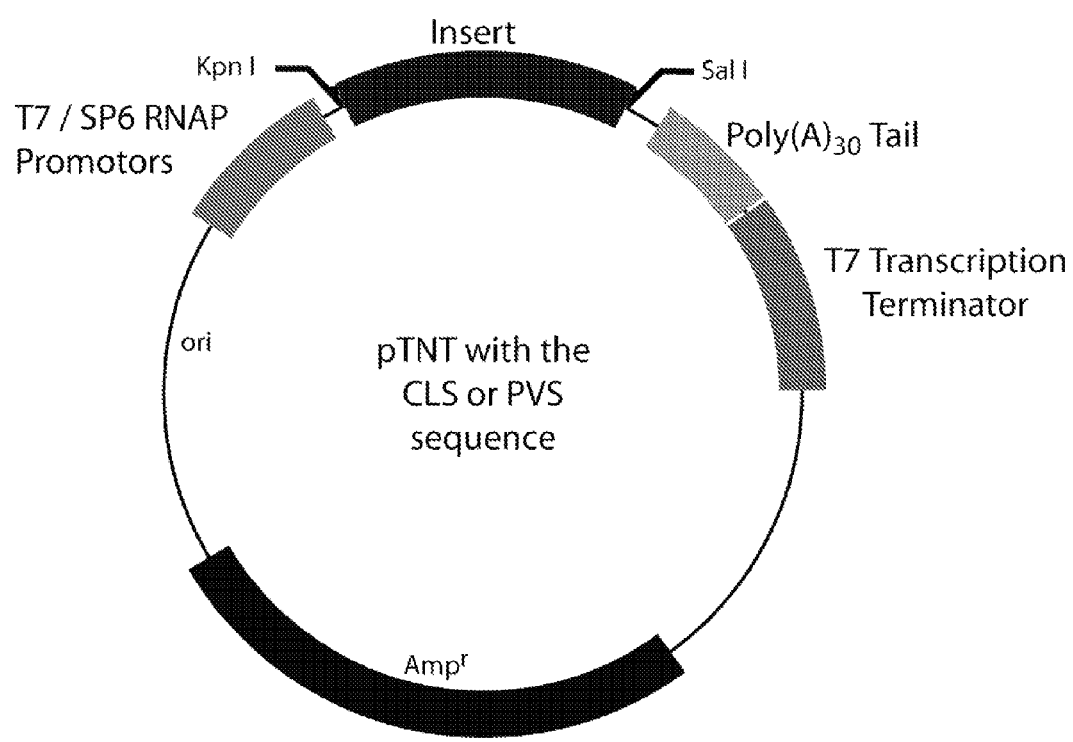
FIG. 1A shows the PCR product was digested and cloned into the Kpn I and Sal I sites of vector pTNT. The region spanning the T7 promoter, insert, poly A, and the T7 terminator were amplified by PCR, resolved on a 1.5% agarose gel, and extracted.

The present invention is directed to addressing the problems of prior art calibrator polynucleotides. As provided herein, the present invention addresses the problems of the prior art by providing calibrator polynucleotides having sequences which are evolutionary unrelated to humans or nucleic acid sequences that are found in samples obtained from humans, e.g. nucleic acid of viruses and microorganisms which infect humans.

Prior to the present invention, avoiding cross reactivity of primers and/or probes of calibrator polynucleotides with nucleic acid sequences from humans or organisms that infect humans could only be achieved by a single method—that is using high-stringency assay conditions. These high stringency assay conditions reduce, but do not eliminate, the probability of interaction between the primers and/or probes in use and any potentially similar sequences in the sample under study. While high stringency conditions can be used with this invention, the present invention prevents or reduces cross reactivity by an entirely different mechanism—the use of evolutionarily distinct polynucleotide sequences.

Prior to the present invention, a random sequence generator was expected to generate polynucleotide sequences that could be used successfully used as calibrator polynucleotides. Unfortunately, it was found that the randomly generated polynucleotide sequences shared an unacceptable degree of similarity to sequences from humans or organisms that infect humans. Polynucleotide sequences from organisms seemingly unrelated to humans and organisms that infect humans were also surprisingly found to share an unacceptable degree of similarity to sequences from humans or organisms that infect humans.

As provided herein, polynucleotides sequences from plant viroids, bacterial type II (group II) introns, and chloroplast type II introns were selected and evaluated for their suitability as calibrator polynucleotides. Sequences from plant viroids were selected because they are unique sub-viral entities that infect plants, have life cycles and molecular mechanisms that are vastly dissimilar to humans or organisms that infect humans, and evolutionary selective pressure continues to maintain the dissimilarities. Likewise, group II (or type II) introns were selected because they are believed to originate from autonomous genetic entities similar to viroids. Group II introns are found in the organellor genomes of plants, lower eucaryotes, and bacteria, but are not found in higher eucaryotes or nuclear genomes (including humans). Although humans have related mitochondrial and nuclear elements, group II introns confer biological functions not found in humans.

As provided herein, polynucleotide sequences from autonomous genetic entities (e.g. viroids) or sequences derived from other elements that originated as autonomous genetic entities (e.g. group II introns) possess sufficient uniqueness and dissimilarlity to sequences from humans and organisms that infect humans such that they are suitable for use as calibrator polynucleotides and controls in a wide variety of assays involving sequences from humans or organisms which infect humans.

The present invention provides polynucleotides which may be used as standards or normalization controls in qualitative and quantitative nucleic acid assays including nucleic acid hybridization assays, quantitative real-time polymerase chain reaction (Q-PCR) assays, cDNA and oligonucleotide microarray assays, Northern blotting, RNase protection assays, and the like and methods of using thereof The present invention also provides polynucleotides which may be used as universal negative controls in an unlimited number of nucleic acid-based assays known in the art, including DNA footprinting, electrophoretic mobility shift assays (EMSA), Rapid Amplification of cDNA Ends (RACE), and the like, and methods of using thereof The polynucleotides of the present invention may be detected or quantified according to methods known in the art including fluoresecence resonance energy transfer (FRET), capillary electrophoresis, colorimetric staining, fluorescent staining, densitometry, fluorometry, and the like.

The polynucleotides of the present invention may be commercialized and validated as universal externally-applied (exogenous) calibrator polynucleotides for various nucleic acid-based assays.

In some embodiments, the polynucleotides of the present invention comprise a target sequence flanked by a forward primer (at the 5' end) and a reverse primer (at the 3' end). As exemplified herein, some preferred target sequences of the present invention are:
PVS Target:

```
PVS target:
                                         (SEQ ID NO: 1)
5' CTGTCGCTTCGGCTACTACCCGGTG 3'
``` or the complementary sequence thereof; and
CLS Target:

```
CLS target:
                                         (SEQ ID NO: 2)
5' AGATGCGTTCCGCTTTACAACTAACGAACA 3'
``` or the complementary sequence thereof.

As used herein, a primer refers to a small synthetic single-stranded nucleic acid molecule that anneals or selectively hybridizes to a selected template nucleic acid sequence and serves as a starting point for nucleic acid replication. A forward primer is complementary or substantially complementary to the beginning of a nucleic acid sequence to be replicated and directs sense strand replication. A reverse primer is complementary or substantially complementary to the end of a nucleic acid sequence to be replicated and directs antisense strand replication. Any suitable primers known in the art may be used in accordance with the present invention. In some embodiments, the length of the primers range from about 15 to about 25 nucleotides, preferably about 17 to about 25 nucleotides, more preferably about 19 to about 25 nucleotides, most preferably about 23 to about 25 nucleotides. In some embodiments, the primer is 18 nucleotides or more in length. Other primers that may be readily constructed or applied in accordance with the present invention by those skilled in the art are contemplated herein.

As used herein, the phrase "selectively (or specifically) hybridizes to" refers to the binding, duplexing, or hybridizing of a nucleic acid molecule to a particular nucleotide sequence only in a sample comprising other nucleic acid molecules under moderate hybridization to stringent hybridization conditions. For selective or specific hybridization, a positive signal is at least about 2 times, preferably about 5 times, more preferably about 10 times the background hybridization. Moderate hybridization conditions are about 10° C. below the thermal melting temperature (Tm) of the probe to about 20° C. to about 25° C. below Tm. Stringent hybridization conditions are about 5° C. below the thermal melting temperature (Tm) of the probe to about 10° C. below Tm.

The hybridization conditions may be less stringent than the conditions exemplified herein. For example, the magnesium chloride concentration, temperature, and the like may be modified according to methods known in the art in order to make the conditions less stringent. It should be noted, however, that the changes in stringency may affect assay sensitivity and specificity. Thus, in some embodiments, the hybridization conditions are stringent hybridization conditions.

As used herein, "substantially complementary" refers to a sequence which is not 100% identically, but specifically hybridizes, to a sequence under moderate, preferably stringent, hybridization conditions.

In some embodiments, an intervening polynucleotide may be located between the forward primer and the 5' end of the target sequence, the reverse primer and the 3' end of the target sequence, or both. The length of the intervening polynucleotide may be any suitable length. As provided herein, a suitable length is one which does not interfere with the intended function of the target sequence. Where a first intervening polynucleotide is between forward primer and the 5' end of the target sequence and a second intervening polynucleotide is between the reverse primer and the 3' end of the target sequence, the intervening polynucleotides may be the same or different. However, in some embodiments, the first and second intervening polynucleotides are incapable of selectively hybridizing with each other. In some embodiments, the intervening polynucleotide does not have a sequence which is capable of selectively hybridizing with the target sequence or its complementary sequence.

Examples of polynucleotides of the present invention include the following (the target sequence is provided in bold, the intervening polynucleotides are in regular font, and the primers are underlined):

```
                                         (SEQ ID NO: 3)
5' GGAGTAATTCCCGCCGAAACAGGGTTTTCCTGTCGCTTCGGCTAC

TACCCGGTGGAAACAACTGAAGCTCCCGAGAACCG 3';

(SEQ ID NO: 4)
5' GAACTCCCGGAATTGATGGAATTATCTGGTAGATGCGTTCCGCTT

TACAACTAACGAACAAGGGCTACAAGTACATTCGAAAGAAGAACGGTA

AA 3';

(SEQ ID NO: 5)
5' GGAGTAATTCCCGCCGAAACAGGGTTTTCACCCTTCCTTTNTTCG

GGTGTCCTTCCTCGCGCCCGCAGGACCACCCCTCGCCCCTTTGCGCTG

TCGCTTCGGCTACTACCCGGTGGAAACAACTGAAGCTCCCGAGAACC

G 3';
and
                                         (SEQ ID NO: 6)
5' GAACTCCCGGAATTGATGGAATTATCTGGTCATCGTCGGCAGAT

AAGATGCGTTCCGCTTTACAACTAACGAACAAGGGCTACCGTGCAAA

ACCATTAACACGAAAGTACATTCGAAAGAAGAACGGTAAA 3'
```

In some embodiments, a flanking polynucleotide may be located at the 5' end of the forward primer, the 3' end of the reverse primer, or both. The length of the flanking polynucleotide may be any suitable length. As provided herein, a suitable length is one which does not interfere with the intended function of the target sequence. Where a first flanking polynucleotide is at the 5' end of the forward primer and a second flanking polynucleotide is at the 3' end of the reverse primer, the flanking polynucleotides may be the same or different. However, in some embodiments, the first and second flanking polynucleotides are incapable of selectively hybridizing with each other. In some embodiments, the flanking polynucleotide does not have a sequence which is capable of selectively hybridizing with the target sequence or its complementary sequence.

Examples of polynucleotides according to the present invention which have flanking polynucleotides include the following (the target sequence is provided in bold, the intervening polynucleotides are in regular font, the primers are underlined and the flanking polynucleotides are italicized):

(SEQ ID NO: 7)
5' CGGAACTAAACTCGTGGTTCCTGTGGTTCACACCTGACCTCCTGA

GCAGAAAAGAAAAAGAATTGCGGCTCGGAGGAGCGCTTCAGGGCATC

CCCGGGGAAACCTGGAGCNAACTGGCAATAAGGCGGTGGGAAGTGGCC

AACGGNCGACAGGAGTAATTCCCGCCGAAACAGGGTTTTCACCCTTCC

TTTNTTCGGGTGTCCTTCCTCGCGCCCGCAGGACCACCCCTCGCCCCT

TTGCGCTGTCGCTTCGGCTACTACCCGGTGGAAACAACTGAAGCTCCC

GAGAACCGCTTTTTCTCTATCTTCCTTGCTTCGGGGCGAGGGTGTTTA

GCCCTTGGAACCGCAGTTGGTTCCT 3';
and (SEQ ID NO: 8)
5' AAGCATTGATTGGAAAAGAGTTAAAGAAGTTGTTAATAACCTTCA

GTCTCGAATTGCAAGTGCAGCTAAGAACGGAAAATGGATAACCGTGAA

CAAACTCTCCCGTCTTCTGACCCGGTCCTTATATGCCAAACTACTTTC

AGTTCGTAAAGTAACCACTAACAAGGGAAGCCGAACTCCCGGAATTGA

TGGAATTATCTGGTCATCGTCGGCAGATAAGATGCGTTCCGCTTTACA

ACTAACGAACAAGGGCTACCGTGCAAAACCATTAACACGAAAGTACAT

TCGAAAGAAGAACGGTAAACTACGACCTCTTAGCATACCAACTATGTA

TGACAGAGCAATGCAAACCCTGCACTCTCTGGTGCTAGGTCCAATCGA

ATCTGCTATAGGTGACAAGACTTCGTTTGGGTTTAAACCTTACCGCTC

AACTAAAGATGCTTACGCCTACCTTCACATCTGTTTAAGCAAGAAAAT

TGCTCCTGAATGGATTGTCGAAGGTGATATTAAAGCCTGCTTTGATGA

AATCAACCACACTTGGATACTTGACAACATCCCTATGGATAAACGAAT

CCTTAAGGAGTTTCTAAAAGCCGGATATGTCGAGAATTATCATCTGTT

TC 3'

Therefore, in some embodiments, the polynucleotides of the present invention comprise a target sequence which may further comprise at least one primer, at least one intervening polynucleotide, at least one flanking polynucleotide, or a combination thereof. In some embodiments, the polynucleotides of the present invention consists of a target sequence and at least one primer. In some embodiments, the present invention consists of a target sequence, at least one primer, and at least one intervening polynucleotide. In some embodiments, the present invention consists of a target sequence, at least one primer, at least one intervening polynucleotide, and at least one flanking polynucleotide.

The polynucleotides of the present invention are derived from known viroid polynucleotides, bacterial chloroplast-like type II intron polynucleotides or chloroplast type II introns. See Table 1.

TABLE I

| Apscaviroid |
|---|
| D12823, Y18035, Y18036, Y18037, Y18038, Y18039, Y18040, Y18041, Y18042, Y18043, Y18044, NC_001830, AY508474, DQ146343, DQ146342, DQ146341, DQ146340, DQ146339, DQ146337, DQ146336, DQ186641, DQ198084, DQ186640, DQ146338, J04348, NC_003612, DQ377132, DQ377131, DQ377130, DQ377129, DQ377128, DQ377125, DQ377126, DQ377127, DQ377124, X06904, Z17225, X87905, X87906, X87907, X87908, X87909, X87915, X87916, X87917, X87918, X87919, X87920, X87921, X87922, X87910, X87911, X87912, X87913, X87914, AB028465, AF059712, NC_001920, AF462167, AF462166, AF462165, AF462164, AF462163, AF462162, AF462161, AF462160, AF462159, AF462158, AF462157, AY639607, AY639606, AB222865, DQ408542, DQ371470, DQ371473, DQ371472, DQ371477, DQ371471, DQ371468, DQ371467, DQ371466, DQ371465, DQ371464, DQ371462, DQ371474, DQ371463, DQ371475, DQ371476, DQ371469, S76452, S75465, AF123879, AF123878, AF123877, AF123876, AF123875, AF123874, AF123873, AF123872, AF123871, AF123870, AF123869, AF123868, AF123867, AF123866, AF123865, AF123864, AF123863, AF123860, AF123859, AF123858, AB054619, AB054620, AB054621, AB054622, AB054623, AB054624, AB054625, AB054626, AB054627, AB054628, AB054629, AB054630, AB054631, AB054632, AF416552, AF416553, AF416374, AF434680, AF447787, AF447786, AF447785, AF447784, AF447783, AF447782, AF447781, AF447780, AF447779, AF447778, AF447788, AF447789, NC_003264, AF458773, AF458774, AF482949, AF482950, AF184147, AF184148, AF184149, AF540967, AF540966, AF540965, AF540964, AY514448, AJ630358, AJ630357, AJ630356, NC_005821, M74065, U21125, AB006734, AB006735, AB006736, AF040721, AF040722, AF428052, AF428053, AF428054, AF428055, AF428056, AF428057, NC_001651, NC_001907, AB054636, AB054637, AY226164, AY226163, AY226162, AY226161, AY226160, AY226159, AY226158, AY226157, AY226156, X17101, NC_003553, DQ362909, DQ362915, DQ362914, DQ362912, DQ362913, DQ362911, DQ362910, DQ362908, X99487, NC_003463, M36646, Y00435, X17696, X71599, NC_001340, AF421195, AJ783357, AY972082, DQ362906, DQ362907, E29032, E29033, NC_003777, AB104531, AB104532, AB104533, AB104534, AB104535, AB104536, AB104537, AB104538, AB104539, AB104540, AB104541, AB104542, AB104543, AB104544, AB104545, AB104546, AB104547, AB104548, AB104549, AB104550, AB104551, AB104552, AB104553, AB104554, AB104555, AB104556, AB104557, AB104558, AB019509, AB054638, AB054639, AB054640, AB054641, E36217, E36218, NC_004358, AB019508, AB054600, AB054601, AB054602, AB054603, AB054604, NC_004359, E36209, E36210, and the like. |
| Pospiviroid |
| K00817, NC_001558, K00818, X06390, X95293, NC_001553, AY062121, DQ144506, M16826, M38345, M36163, M14814, M25199, X58388, M88681, M88678, M88677, X17268, X52036, X52037, X52039, X52038, X52040, M93685, V01465, X76845, X76846, X76844, X76848, X76847, Z34272, U23060, U23059, U23058, U51895, X97387, Y09382, Y09383, |

TABLE I-continued

Y08852, Y09381, Y09577, Y09576, Y09575, Y09574, Y09889, Y09888, Y09887, Y09886,
Y09890, Y09891, AJ007489, AF369530, NC_002030, E00278, AF454395, AF459004,
AF459003, AF459002, AF459001, AF459000, AF458999, AF458998, AF458997, AF458996,
AF458995, AF458994, AF458993, AF458992, AF458991, AF458990, AF458989, AF458988,
AF458987, AF458986, AF459007, AF459006, AF459005, AF483470, AF483471, AF483472,
AF483473, AY152841, AY152840, AJ515261, AY360446, AJ583449, AY492075, AY492076,
AY492077, AY492078, AY492079, AY492080, AY492081, AY492082, AY492083, AY492084,
AY493559, AY493560, AY518939, AY518940, AY532801, AY532802, AY532803, AY532804,
AY372400, AY372394, AY372398, AY372397, AJ634596, AY673974, AY937179, AY937187,
AY937186, AY937185, AY937194, AY937193, AY937192, AY937184, AY937191, AY937190,
AY937189, AY937183, AY937182, AY937188, AY937181, AY937180, AY962324,
DQ315388, L78454, L78456, L78457, L78458, L78459, L78460, L78461, L78463, L78462,
NC_003637, X95734, NC_003613, DQ094293, DQ094294, X15663, M93686, X95292,
NC_003538, AY222078, AY222077, AY222076, AY222075, AY222074, AY222073,
AY222072, AY365230, AY372396, AY372395, AY373446, AY372392, AY367350,
DQ076250, DQ061192, DQ022677, DQ061193, EF015581, DQ923061, DQ923060,
DQ923058, DQ923059, J02053, M34917, K00964, K00965, M30870, M30869, M30871,
M30868, local: CEVd.19, local: CEVd.20, local: CEVd.21, Y00328, X53716, S67446, S67442,
S67441, S67440, S67438, S67437, U21126, S79831, AF298177, AF298178, AF428058,
AF428059, AF428060, AF428061, AF428062, AF428063, AF428064, AF434678, AF148717,
NC_001464, AB054592, AB054593, AB054594, AB054595, AB054596, AB054597,
AB054598, AB054599, AF458771, AF458772, AF458775, AF458776, AJ490825, AY229990,
AJ564803, AJ564802, AJ564801, AJ564800, AJ564799, AJ564798, AJ564797, AJ564796,
AJ564795, AF540963, AF540962, AF540961, AF540960, AY456136, AY514446, AY517494,
AY517496, AY517495, AY514444, AY514445, AY514447, AY523582, AY523584, AY523583,
AY671957, AY671956, AY671955, AY671954, AY671953, AY671952, AY372390, AY372393,
AY372391, DQ094297, DQ094296, DQ094295, AY513268, DQ831486, DQ831485,
DQ444474, DQ400342, DQ471996, DQ471995, DQ471994, DQ444473, DQ431996,
DQ431991, DQ431995, DQ431993, DQ431992, DQ431994, DQ846884, DQ846885, V01107,
M19506, Z68201, U82445, AJ001853, AJ001852, AJ001851, AJ001850, AJ001849, D88895,
AF394452, AF394453, AJ000046, AB006737, E13156, NC_002015, AB055974, E50939,
X16407, X16408, X16409, AJ585258, DQ094298, AJ969017, AB255880, AB255879,
AB279771, AB279770, AB279769, AB279768, AF162131, NC_000885, AY372399
Cocadviroid X07397, AJ290404, AJ290405, AJ290406, AJ290407, AJ290408, AJ290409, AJ290410,
AJ290411, AJ290412, NC_003611, M20731, local: CTiVd.2, NC_001471, J02049, J02050,
J02051, E00277, NC_001462, DQ097183, DQ097184, DQ097185, X14638, AB054633,
AB054634, AB054635, NC_003539, AJ630361, AJ630360, AJ630359
Hostuviroid AJ011813, AJ011814, Y08438, Y08437, Y09345, Y09346, Y09344, Y09347, Y09348,
Y09349, AJ297825, AJ297826, AJ297827, AJ297828, AJ297829, AJ297830, AJ297831,
AJ297832, AJ297833, AJ297834, AJ297835, AJ297836, AJ297837, AJ297838, AJ297839,
AJ297840, AY460201, DQ362905, DQ362904, DQ362901, DQ648601, DQ648600,
DQ362903, DQ362902, DQ362900, X06718, X06719, X13838, U02527, AF131248,
AF131249, AF131250, AF131251, AF131252, AF213483, AF213484, AF213485, AF213486,
AF213487, AF213488, AF213489, AF213490, AF213491, AF213492, AF213493, AF213494,
AF213495, AF213496, AF213497, AF213498, AF213499, AF213500, AF213501, AF213502,
AF213503, AF359276, AF359275, AF359274, AF359273, AF359272, AF359271, AF359270,
X69519, X69518, AF416554, AF416555, AF416556, AF416557, AF434679, AB054605,
AB054606, AB054607, AB054608, AB054609, AB054610, AB054611, AB054612, AB054613,
AB054614, AB054615, AB054616, AB054617, AB054618, AB055634, NC_001351,
AF517563, AJ490824, AY143170, AY143169, AY143168, AY143167, AY379533, AY379534,
AY379535, AY379536, AY379537, AY379538, AY379539, AY379540, AY379541, AY513267,
AY532933, AY532934, AY532935, AY536521, DQ014517, DQ014515, DQ014514,
DQ014516, AY594207, AY594201, AY594203, AY594200, AY594202, AY594204,
AY735993, AY735994, AY735992, AY735991, AY237168, NC_003881, AY594209,
AY594205, AY594208, AY594206, AB211243, AB211242, X00524, X07405, M35717,
X06873, X15330, X87924, X87923, X87925, X87926, X87927, X87928, Y14050, AB039272,
AB039271, AB039270, AB039269, AB039268, AB039267, AB039266, AB039265, AF462156,
AF462155, AF462154, DQ444476, DQ444475, DQ471998, DQ471997, DQ023269,
AB222864, AB219944, AB219946, AB219945, AB219944, AB219943, AB219942,
DQ371459, DQ371457, DQ371458, DQ371456, DQ371454, DQ371451, DQ371453,
DQ371452, DQ371455, DQ371439, DQ371438, DQ371449, DQ371448, DQ371447,
DQ371450, DQ371446, DQ371436, DQ371437, DQ371434, DQ371445, DQ371432,
DQ371433, DQ371435, DQ371444, DQ371443, DQ371442, DQ371441, DQ371440, X00009,
X12537, E01844, E01843, E01842, E00276, AF100641, D13765, D13764, Y09352, Y09351,
Y09350, Y09343, AB098502, AB098501, AB098500, AY425170, AY425171, AY460202,
AY189685
Coleviroid X95364, X57294, X95290, NC_003683, X95365, X97202, NC_003682, X52960, X69293,
X95291, X95366, NC_003681, DQ178398, DQ178397, DQ178399, DQ178396, DQ178395,
NC_003882
Pelamoviroid Y14700, AJ247112, AJ247113, AJ247114, AJ247115, AJ247116, AJ247117, AJ247118,
AJ247119, AJ247120, AJ247121, AJ247122, AJ247123, NC_003540, AB181858, AB181857,
AB181860, AB181859, AJ878089, AJ878088, AJ878087, AJ878085, AJ878086, DQ450682, TABLE I-continued DQ402041, M83545, AJ005294, AJ005295, AJ005296, AJ005297, AJ005298, AJ005299,
AJ005300, AJ005301, AJ005302, AJ005303, AJ005304, AJ005305, AJ005306, AJ005307,
AJ005308, AJ005309, AJ005310, AJ005311, AJ005312, AJ005313, AJ005314, AJ005315,
AJ005316, AJ005317, AJ005318, AJ005319, AJ005320, AJ005321, AJ005322, AF170496,
AF170497, AF170498, AF170499, AF170500, AF170501, AF170502, AF170503, AF170504,
AF170505, AF170506, AF170507, AF170508, AF170509, AF170510, AF170511, AF170512,
AF170513, AF170514, AF170515, AF170516, AF170517, AF170518, AF170519, AF170520,
AF170521, AF170522, AF170523, AJ241818, AJ241819, AJ241820, AJ241821, AJ241822,
AJ241823, AJ241824, AJ241825, AJ241826, AJ241827, AJ241828, AJ241829, AJ241830,
AJ241831, AJ241832, AJ241833, AJ241834, AJ241835, AJ241836, AJ241837, AJ241838,
AJ241839, AJ241840, AJ241841, AJ241842, AJ241843, AJ241844, AJ241845, AJ241846,
AJ241847, AJ241848, AJ241849, AJ241850, AF339739, AF339740, AF339741, AF339742,
NC_003636, AJ550545, AJ550912, AJ550911, AJ550910, AJ550909, AJ550908, AJ550907,
AJ550906, AJ550905, AJ550904, AJ550903, AJ550902, AJ550901, AJ550900, AJ550899,
AJ550898, AY685181, DQ222061, DQ222060, DQ222059, DQ222058, DQ222057,
DQ222056, DQ222055, DQ222054, DQ222053, DQ222052, DQ222051, DQ222050,
DQ222049, DQ222048, DQ222047, DQ222046, DQ222045, DQ222044, DQ222043,
DQ222069, DQ222068, DQ222066, DQ222065, DQ222067, DQ222064, DQ222063,
DQ222084, DQ222083, DQ222082, DQ222081, DQ222080, DQ222079, DQ222078,
DQ222077, DQ222062, DQ222097, DQ222096, DQ222091, DQ222090, DQ222089,
DQ222095, DQ222094, DQ222088, DQ222087, DQ222093, DQ222092, DQ222086,
DQ222085, DQ222076, DQ222075, DQ222074, DQ222073, DQ222072, DQ222071,
DQ222070, DQ222104, DQ222103, DQ222102, DQ222101, DQ222100, DQ222099,
DQ222098, DQ839565, DQ839564
Avsunviroid J02020, X13000, S73860, M27297, M31100, M31086, M31085, M31087, M31092, M31088,
M31093, M31089, M31094, M31090, M31095, M31091, M31096, M31097, M31098, M31099,
S73861, S74687, AF229815, AF229816, AF229817, AF229818, AF229819, AF229820,
AF229821, AF229822, AF229823, AF229824, AF229825, AF229826, AF229827, AF229828,
NC_001410, AF404029, AF404030, AF404031, AF404032, AF404033, AF404034,
AF404035, AF404036, AF404037, AF404038, AF404039, AF404040, AF404041, AF404042,
AF404043, AF404044, AF404045, AF404046, AF404047, AF404048, AF404049, AF404050,
AF404051, AF404052, AF404053, AF404054, AF404055, AF404056, AF404057, AF404058,
AF404059, AF404060, AF404061, AF404062, AF404063, AF404064, AF404065, AF404066,
AF404067, AF404068, AF404069, AF404070, AF404071, AF404072, AF404073, AF404074,
X52041, X52042, X52043, X52044, X52045
Unassigned NC_004728, AJ536620, AJ536619, AJ536618, AJ536617, AJ536616, AJ536615, AJ536614,
AJ536613, AJ536612
Bacterial Chloroplast-like Type II Introns AY057439 (1648-4444), NZ_AAAD01000090 (244262-246454), AF065404 (6445-8975),
AE017006 (206804-209162), AF142677 (34045-36400), AE016935 (158836-161240),
X71404 (446-2898), AF074613 (58241-60646), AP006568 (168850-171364),
NZ_AAAN01000223 (11998-14165), NZ_AAAN01000049 (204-2130), NZ_AABC01000200
(59260-61448), AP003599 (30736-33044), AP003600 (259212-261419), AP003600 (258243-
262762), AP003604 (45422-47907), Y18999 (752-2957), NZ_AAAI01000185 (4523-7467),
AP002086 (134014-136195), AP005369 (27344-30566), AP005369 (27972-28810),
AP005369 (91363-93748), AP005369 (219750-220594), AP005369 (245778-246623),
AP005369 (293406-296628), AP005369 (294034-294872), AP005370 (143581-145264),
AP005370 (144222-145060), AP005371(25104-27488), AP005372 (123210-126437),
AP005372 (140298-141142), AP005372 (247889-251113), AP005372 (248517-249355),
AP005372 (258835-259672), AP005372 (296704-299926), AP005372 (297332-298170),
AP005374 (77764-78613), AP005374 (183246-184091), AP005375 (281140-281978),
AP005376 (69318-70167), AP005377 (63987-64831), AP005377 (163437-164281),
NZ_AAAU01000028 (50472-52964), NZ_AAAU01000028 (53010-55530),
NZ_AAAU01000003 (47249-49774), NZ_AAAU01000003 (51979-54532),
NZ_AAAU01000001 (207867-210242), NZ_AAAU01000018 (84323-86946),
NZ_AAAU01000012 (121800-126923), NZ_AAAU01000012 (124307-126770),
NZ_AAAU01000012 (128050-132040), AF382392 (3712-6232), AE003999 (10976-13380),
AE011073(4279-6431), AE011185(1722-5744), AE011130(2228-6247), AE010882(4828-
5781), AE011106(4446-5200), AE010996(801-1555), AE013515 (3337-5483), AE013516
(7432-10327)
Chloroplast Type II Introns Fragment 1 of Intron 1 in *Euglena gracilis* psbF gene
Fragment 2 of Intron 1 in *Euglena gracilis* psbF gene
Fragment 2 of Intron 1 in *Euglena gracilis* rps3 gene
Fragment 3 of Intron 1 in *Euglena gracilis* psbF gene
Intron 1 in *Bryopsis maxima* rbcL intron
Intron 1 in *Euglena gracilis* rpl22 gene
Intron 1 in *Euglena gracilis* rpoC2 gene
Intron 1 in *Euglena gracilis* rps3 gene
Intron 1 in *Euglena gracilis* rps8 gene
Intron 1 in *Euglena gracilis* atpA gene
Intron 1 in *Euglena gracilis* atpB gene
Intron 1 in *Euglena gracilis* atpE gene
Intron 1 in *Euglena gracilis* atpF gene TABLE I-continued Intron 1 in *Euglena gracilis* psaA gene
Intron 1 in *Euglena gracilis* psaB gene
Intron 1 in *Euglena gracilis* psbA gene
Intron 1 in *Euglena gracilis* psbB gene
Intron 1 in *Euglena gracilis* psbD gene
Intron 1 in *Euglena gracilis* psbE gene
Intron 1 in *Euglena gracilis* psbF gene
Intron 1 in *Euglena gracilis* psbT gene
Intron 1 in *Euglena gracilis* rbcL gene
Intron 1 in *Euglena gracilis* ycf4 gene
Intron 1 in *Euglena viridis* psbC gene
Intron 1 in *Nicotiana tabacum* atpF gene
Intron 1 in *Nicotiana tabacum* clpP gene
Intron 1 in *Nicotiana tabacum* ndhA gene
Intron 1 in *Zea mays* atpF gene
intron 1 in *Oenothera atrovirens* trnA gene
intron 1 in *Oenothera atrovirens* trnI gene
Intron 2 in *Euglena gracilis* rpl16 gene
Intron 2 in *Euglena gracilis* rpoC2 gene
Intron 2 in *Euglena gracilis* atpA gene
Intron 2 in *Euglena gracilis* atpB gene
Intron 2 in *Euglena gracilis* atpE gene
Intron 2 in *Euglena gracilis* atpF gene
Intron 2 in *Euglena gracilis* psaA gene
Intron 2 in *Euglena gracilis* psaB gene
Intron 2 in *Euglena gracilis* psbA gene
Intron 2 in *Euglena gracilis* psbC gene
Intron 2 in *Euglena gracilis* psbD gene
Intron 2 in *Euglena gracilis* psbE gene
Intron 2 in *Euglena gracilis* rbcL gene
Intron 2 in *Euglena gracilis* rps9 gene
Intron 2 in *Euglena viridis* psbC gene
Intron 2 in *Glycine max* rps12 gene
Intron 2 in *Marchantia polymorpha* rps12 gene
Intron 2 in *Nicotiana tabacum* clpP gene
Intron 2 in *Zea mays* rps12 gene
Intron 3 in *Euglena gracilis* rps8 gene
Intron 3 in *Euglena gracilis* atpB gene
Intron 3 in *Euglena gracilis* atpF gene
Intron 3 in *Euglena gracilis* psaA gene
Intron 3 in *Euglena gracilis* psaB gene
Intron 3 in *Euglena gracilis* psbA gene
Intron 3 in *Euglena gracilis* psbB gene
Intron 3 in *Euglena gracilis* psbC gene
Intron 3 in *Euglena gracilis* psbD gene
Intron 3 in *Euglena gracilis* rbcL gene
Intron 4 in *Euglena gracilis* rps2 gene
Intron 4 in *Euglena gracilis* atpB gene
Intron 4 in *Euglena gracilis* psaB gene
Intron 4 in *Euglena gracilis* psbA gene
Intron 4 in *Euglena gracilis* psbB gene
Intron 4 in *Euglena gracilis* psbD gene
Intron 5 in *Euglena gracilis* psaB gene
Intron 5 in *Euglena gracilis* psbC gene
Intron 5 in *Euglena gracilis* psbD gene
Intron 6 in *Euglena gracilis* rpoC1 gene
Intron 6 in *Euglena gracilis* psaB gene
Intron 6 in *Euglena gracilis* psbC gene
Intron 6 in *Euglena gracilis* psbD gene
Intron 6 in *Euglena gracilis* rps9 gene
Intron 7 in *Euglena gracilis* psbC gene
Intron 7 in *Euglena gracilis* psbD gene
Intron 8 in *Euglena gracilis* rpoB gene
Intron in *Arabidopsis thaliana* ndhA gene
Intron in *Arabidopsis thaliana* atpF gene
Intron in *Arabidopsis thaliana* ndhB gene
Intron in *Arabidopsis thaliana* petB gene
Intron in *Arabidopsis thaliana* petD gene
Intron in *Arabidopsis thaliana* rpl16 gene
Intron in *Arabidopsis thaliana* rpoC1 gene
Intron in *Arabidopsis thaliana* rps12 gene
Intron in *Arabidopsis thaliana* rps16 gene
Intron in *Arabidopsis thaliana* trnA gene
Intron in *Arabidopsis thaliana* trnG gene
Intron in *Arabidopsis thaliana* trnK gene
Intron in *Euglena gracilis* ccsA gene
Intron in *Euglena gracilis* petG gene
Intron in *Glycine max* trnA gene
Intron in *Marchantia polymorpha* atpF gene
Intron in *Marchantia polymorpha* ndhA gene

TABLE I-continued

Intron in *Marchantia polymorpha* ndhB gene
Intron in *Marchantia polymorpha* petB gene
Intron in *Marchantia polymorpha* petD gene
Intron in *Marchantia polymorpha* ropC1 gene
Intron in *Marchantia polymorpha* rpl16 gene
Intron in *Marchantia polymorpha* trnA gene
Intron in *Marchantia polymorpha* trnG gene
Intron in *Marchantia polymorpha* trnI gene
Intron in *Marchantia polymorpha* trnK gene
Intron in *Marchantia polymorpha* trnV gene
Intron in *Triticum aestivum* atpF gene
Intron in *Triticum aestivum* trnG gene
Intron in *Zea mays* ndhA gene
Intron in *Zea mays* ndhB gene
Intron in *Zea mays* petB gene
Intron in *Zea mays* petD gene
Intron in *Zea mays* rpl2 gene
Intron in *Zea mays* rps16 gene
Intron in *Zea mays* trnG gene
Intron in *Zea mays* trnI gene
Intron in *Zea mays* trnK gene
Intron in *Zea mays* trnV gene
Intron in *Zea mays* trnV gene
ORF135 in *Marchantia polymorpha*

* In order to reduce extra page fee costs the sequences provided in this table are known in the art and readily available. For example, see the World Wide Web at fp.ucalgary.ca/group2introns/species.htm, (hypertext transfer protocol://) web.austin.utexas.edu/fugoid/introndata/main.htm, and (hypertext transfer protocol://) subviral.med.uottawa.ca/cgi-bin/home.cgi. These sequences are also set forth in the provisional priority document. The exclusion of the sequences in this table is not to be interpreted as a disclaimer of subject matter.

Thus, nucleic acid molecules of the present invention include sequences comprising, preferably consisting of, 18 to about 620, preferably 18 to about 200, more preferably 18 to about 150, most preferably 18 to about 100, consecutive nucleotides of any one of the sequences identified in Table 1, SEQ ID NO:7, SEQ ID NO:8, or a complementary sequence thereof.

In some embodiments, the nucleic acid sequence of the present invention is selected from the group consisting of SEQ ID NO:1 or its complement thereof; SEQ ID NO:2 or its complement thereof; SEQ ID NO:3 or its complement thereof; SEQ ID NO:4 or its complement thereof; SEQ ID NO:5 or its complement thereof; and SEQ ID NO:6 or its complement thereof; SEQ ID NO:7 or its complement thereof, SEQ ID NO:8 or its complement thereof; SEQ ID NO:9 or its complement thereof; SEQ ID NO:10 or its complement thereof; SEQ ID NO:11 or its complement thereof; and SEQ ID NO:12 or its complement thereof.

In some embodiments, the nucleic acid molecule has a sequence wherein 95% to 100%, preferably 96% to 100%, more preferably 97% to 100%, even more preferably 98% to 100%, most preferably 99% to 100%, of its nucleotides are identical to a sequence selected from the group consisting of SEQ ID NO:1 or its complement thereof; SEQ ID NO:2 or its complement thereof; SEQ ID NO:3 or its complement thereof; SEQ ID NO:4 or its complement thereof; SEQ ID NO:5 or its complement thereof; and SEQ ID NO:6 or its complement thereof; SEQ ID NO:7 or its complement thereof, SEQ ID NO:8 or its complement thereof; SEQ ID NO:9 or its complement thereof; SEQ ID NO:10 or its complement thereof; SEQ ID NO:11 or its complement thereof; and SEQ ID NO:12 or its complement thereof.

Since the sequences of the present invention are not derived from animal or human polynucleotides, they do not exhibit significant sequence homology to known animal or human polynucleotides. Therefore, the polynucleotides of the present invention may be used as calibrator polynucleotides (e.g. standards or controls) in qualitative nucleic acid assays where the polynucleotides being assayed are human or animal origin.

As used herein, "nucleic acid molecule", "polynucleotide", and "oligonucleotide" are used interchangeably to refer DNA and RNA molecules of natural or synthetic origin which may be single-stranded or double-stranded, and represent the sense or antisense strand. The nucleic acid molecules of the present invention may contain known nucleotide analogs or modified backbone residues or linkages, and any substrate that can be incorporated into a polymer by DNA or RNA polymerase. Examples of such analogs include phosphorothioates, phosphoramidates, methyl phosphonates, chiral-methyl phosphonates, 2-O-methyl ribonucleotides, peptide-nucleic acids (PNAs), and the like.

In preferred embodiments, the nucleic acid molecule of the present invention is isolated. As used herein, "isolated" refers to a nucleic acid molecule that is isolated from its native environment. An "isolated" nucleic acid molecule may be substantially isolated or purified from the genomic DNA of the species from which the nucleic acid molecule was obtained. An "isolated" polynucleotide may include a nucleic acid molecule that is separated from other DNA segments with which the nucleic acid molecule is normally or natively associated with at either the 5' end, 3' end, or both.

The nucleic acid molecules of the present invention may be in its native form or synthetically modified. The nucleic acid molecules of the present invention may be single-stranded (coding or antisense) or double-stranded, and may be DNA (genomic, cDNA or synthetic) or RNA molecules. RNA molecules include mRNA molecules, which contain introns and correspond to a DNA molecule in a one-to-one manner, and mRNA molecules, which do not contain introns. The nucleic acid molecules of the present invention may be linked to other nucleic acid molecules, support materials, reporter molecules, quencher molecules, or a combination thereof. Other nucleic acid molecules include promoters, polyadenylation signals, additional restriction enzyme sites, multiple cloning sites, other coding segments, and the like. It is therefore contemplated that a nucleic acid fragment of almost any length may be employed, with the total length preferably being limited by the ease of preparation and use in the intended recombinant DNA or PCR protocol.

The nucleic acid molecules of the present invention may be readily prepared by methods known in the art, for example, directly synthesizing the nucleic acid sequence using methods and equipment known in the art such as automated oligonucleotide synthesizers, PCR technology, recombinant DNA techniques, and the like.

The nucleic acid molecules of the present invention may contain a label. A wide variety of labels and conjugation techniques are known by those skilled in the art and may be used in various nucleic acid and amino acid assays employing the nucleic acid molecules of the present invention. As used herein a "label" or a "detectable moiety" is a composition that is detectable by spectroscopic, photochemical, biochemical, immunochemical, or chemical means. A "labeled" nucleic acid molecule comprises a bound label such that the presence of the nucleic acid molecule may be detected by detecting the presence of the label bound to thereto. The label may be bound to the nucleic acid molecule via a covalent bond, such as a chemical bond, or a noncovalent bond, such as ionic, van der Waals, electrostatic, or hydrogen bonds. Methods known in the art for producing labeled hybridization or PCR probes for detecting sequences related to polynucleotides may be used and include oligolabeling, nick translation, end-labeling or PCR amplification using a labeled nucleotide, and the like, preferably end-labeling. Suitable reporter molecules and quencher molecules that may be used include radionucleotides, enzymes, fluorescent, chemiluminescent, or chromogenic agents as well as substrates, cofactors, inhibitors, magnetic particles, and the like. In preferred embodiments, a fluorescent reporter molecule and quencher molecule are used.

As used herein, a "nucleic acid probe" and "probe" refers to a nucleic acid molecule that is capable of binding to a given nucleic acid molecule (target sequence) having a sequence that is complementary to the sequence of the nucleic acid probe. A probe may include natural or modified bases known in the art. See e.g. MPEP 2422, $8^{th}$ ed., which is herein incorporated by reference. The nucleotide bases of the probe may be joined by a linkage other than a phosphodiester bond, so long as the linkage does not interfere with the ability of the nucleic acid molecule to bind a complementary nucleic acid molecule. The probe may bind a target sequence that is less than 100% complementary to the probe sequence and such binding depends upon the stringency of the hybridization conditions. The presence or absence of the probe may be detected to determine the presence or absence of a target sequence or subsequence in a sample. The probe may contain a label whose signal is detectable by methods known in the art. As used herein a "signal" is a characteristic that is measurable using methods known in the art. Where the label is a reporter molecule and a quencher molecule, the signal may increase or decrease upon dissociation of reporter molecule and the quencher molecule. For example, if the reporter molecule is a fluorophore, separation of the quencher from the fluorophore will generate a detectable signal due to an increase in light energy emitted by the fluorophore in response to illumination.

Primers and probes according to the present invention can be designed using, for example, a computer program such as OLIGO (Molecular Biology Insights, Inc., Cascade, Colo.). Important features when designing oligonucleotides to be used as amplification primers include an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). As with oligonucleotide primers, oligonucleotide probes usually have similar melting temperatures, and the length of each probe must be sufficient for sequence-specific hybridization to occur but not so long that fidelity is reduced during synthesis. In preferred embodiments, the oligonucleotide primers and probes according to the present invention are about 20 to about 45 nucleotides in length, preferably about 25 to about 45 nucleotides in length, more preferably about 30 to about 45 nucleotides in length.

Constructs of the invention include vectors containing the polynucleotides disclosed herein. Constructs of the invention can be used, for example, as control template nucleic acid molecules. Vectors suitable for use in the present invention are commercially available and/or produced by recombinant DNA technology methods routine in the art. The nucleic acid molecules disclosed herein can be obtained, for example, by chemical synthesis, direct cloning, or by PCR amplification. The nucleic acid molecules of the present invention can be operably linked to a promoter or other regulatory element such as an enhancer sequence, a response element, or an inducible element that modulates expression of the nucleic acid molecule.

As used herein, "operably linking" refers to connecting a promoter and/or other regulatory elements to a given nucleic acid molecule in such a way as to permit and/or regulate expression of the nucleic acid molecule. For example, a promoter that does not normally direct expression of a nucleic acid molecule disclosed herein can be used to direct transcription of the nucleic acid molecule using, for example, a viral polymerase, a bacterial polymerase, or a eukaryotic RNA polymerase II. In addition, operably linked can refer to an appropriate connection between the nucleic acid molecule and a heterologous coding sequence, such as a reporter gene, in such a way as to permit expression of the heterologous coding sequence.

Constructs suitable for use in the methods of the invention may also include sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention can be propagated in a host cell. As used herein, "host cell" includes prokaryotes and eukaryotes, such as yeast, plant and animal cells. Prokaryotic hosts may include *E. coli*, *Salmonella* spp., *Serratia* spp. and *Bacillus* spp. Eukaryotic hosts include yeasts such as *S. cerevisiae*, *S. pombe*, *Pichia pastoris*, mammalian cells such as COS cells or Chinese hamster ovary (CHO) cells, insect cells, and plant cells such as *Arabidopsis thaliana* and *Nicotiana tabacum*. Other host cells known in the art may be used according to the present invention.

A construct of the invention can be introduced into a host cell using any of the techniques known to those of ordinary skill in the art, such as calcium phosphate precipitation, electroporation, heat shock, lipofection, microinjection, and viral-mediated nucleic acid transfer. In addition, naked DNA can be delivered directly to cells using methods known in the art. See e.g., U.S. Pat. Nos. 5,580,859 and 5,589,466, which are herein incorporated by reference.

Polymerase chain reaction (PCR) methods known in the art may be used according to the present invention. See e.g., U.S. Pat. Nos. 4,683,202, 4,683,195, 4,800,159, and 4,965,188, which are herein incorporated by reference. Within each thermocycler run, control samples are cycled as well. The polynucleotides of the present invention may be used as positive controls or as standards. When used as a positive control, the polynucleotides containing or consisting of the target sequence are intentionally amplified by the addition of amplification primers along with the polynucleotide of interest. When used as standard, a known amount of a polynucleotide containing or consisting of the target sequence is added to the sample and not intended to be amplified by not adding amplification primers which would cause the target sequence to become amplified.

The nucleic acid molecules of the present invention may be used with fluorescence resonance energy transfer (FRET), Scorpions, and Molecular Beacons assays. See Szollosi, et al. (1998) Cytometry 34(4):159-179; Schweitzer and Kingsmore (2001) Curr. Opin. Biotechnol. 12(1):21-27; and Antony and Subramaniam (2001) J. Biomol. Struct. Dyn. 19(3):497-504, which are herein incorporated by reference.

Fluorescence Resonance Energy Transfer (FRET) methods known in the art may also be used according to the present invention. See e.g., U.S. Pat. Nos. 4,996,143, 5,565,322, 5,849,489, and 6,162,603, which are herein incorporated by reference. As described herein, amplification products can be detected using labeled hybridization probes that take advantage of FRET technology. A common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by a light source. During FRET, the fluorescein transfers its energy to an acceptor fluorescent moiety such as LightCycler™-Red 640 (LC™-Red 640) or LightCycler™-Red 705 (LC™-Red 705). The acceptor fluorescent moiety then emits light of a longer wavelength, which is detected by an optical detection system such as the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules.

Another FRET format utilizes TaqMan® technology to detect the presence or absence of an amplification product. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7500 Sequence Detection System (Applied Biosystems, Foster City, Calif.) uses TaqMan® technology, and is suitable for performing the methods described herein Information on PCR amplification and detection using an ABI PRISM® 7500 system is known in the art.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

PCR methods known in the art may be used in conjunction with FRET technology. In some embodiments, a LightCycler™ instrument or the like is used. The specifications of the LightCycler™ System, methods of using and real-time and on-line monitoring of PCR are known in the art. See WO 97/46707, WO 97/46714 and WO 97/46712, which are herein incorporated by reference.

As an alternative to FRET, an amplification product can be detected using a double-stranded DNA binding dye such as a fluorescent DNA binding dye (e.g., SYBRGreenI® or SYBRGold® (Molecular Probes, Eugene, Oreg.)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

In some embodiments, the methods of the invention include steps to avoid contamination. For example, an enzymatic method utilizing uracil-DNA glycosylase is described in U.S. Pat. Nos. 5,035,996, 5,683,896 and 5,945,313, which are herein incorporated by reference, to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

The present invention further provides kits for use with quantitative nucleic acid assays such as PCR amplification and PCR assays, including TagMan® based assays, fluorescence resonance energy transfer (FRET), Scorpions, and Molecular Beacons assays. See Szollosi, et al. (1998) Cytometry 34(4):159-179; Schweitzer and Kingsmore (2001) Curr. Opin. Biotechnol. 12(1):21-27; and Antony and Subramaniam (2001) J. Biomol. Struct. Dyn. 19(3):497-504, which are herein incorporated by reference. Such kits comprise at least one polynucleotide of the present invention and one or more components necessary for performing the assay. Components may be compounds, reagents, containers, instructions and/or equipment.

The kits may be used for any one or more of the uses described herein, and, accordingly, may contain instructions (written and/or electronic) for any one or more of the following uses: detecting and/or quantifying a given nucleic acid sequence is present in a sample, comparing given nucleic acid sequence to a reference sequence, determining genotype, determining allele composition of a given nucleic acid, detecting and/or quantifying multiple nucleic acid sequences, and use of the methods in conjunction with nucleic acid amplification techniques.

The kits of the invention comprise one or more containers comprising any combination of the components or reagents described herein. For example, in one embodiment, the kit comprises a polynucleotide of the present invention and a set of primers and probes for conducting an assay for a given nucleic acid molecule and/or the target sequence. The kit may further include at least one label and at least one substrate for producing a signal. The kit may further include deoxynucleoside triphosphates and/or ribonucleoside triphosphates. The kit may further include one or more suitable buffers for conducting the given assay. Each component of the kit can be packaged in separate containers or some components can be combined in one container where cross-reactivity and shelf life permit.

As used herein, "sequence identity" in the context of two or more nucleic acid molecules, refers to two or more sequences or subsequences that are the same or have a specified percentage of nucleotide bases that are the same (i.e., 70% identity, optionally 75%, 80%, 85%, 90%, 95%, or more identity over a specified region), when compared and aligned for maximum correspondence over a comparison window, or designated region as measured using one of the following sequence comparison algorithms or by manual alignment and visual inspection. The percentage of sequence identity may be calculated by comparing two optimally aligned sequences over the window of comparison, determining the number of positions at which the identical residues occur in both sequences to yield the number of matched positions, dividing the number of matched positions by the total number of positions in the window of comparison (i.e., the window size), and multiplying the result by 100 to yield the percentage of sequence identity.

Methods of alignment of sequences for comparison are well-known in the art. See e.g. Smith & Waterman (1981) Adv. Appl. Math. 2:482; Needleman & Wunsch (1970) J. Mol. Biol. 48:443; and Pearson & Lipman (1988) PNAS USA 85:2444, which are herein incorporated by reference. Alignment may be conducted using computer programs such as GAP, BESTFIT, FASTA, and TFASTA in the Wisconsin Genetics Software Package (Genetics Computer Group, 575 Science Dr., Madison, Wis.), or manually by visual inspection. See also Feng & Doolittle (1987) J. Mol. Evol. 35:351-360; Higgins & Sharp (1989) CABIOS 5:151-153; and Devereaux et al. (1984) Nuc. Acids Res. 12:387-395, which are herein incorporated by reference.

Alternatively, BLAST and BLAST 2.0 algorithms may be used to determine the sequence identity of two or more sequences. See Altschul et al. (1977) Nuc. Acids Res. 25:3389-3402 and Altschul et al. (1990) J. Mol. Biol. 215: 403-410, which are herein incorporated by reference. BLAST analyses are publicly available through the National Center for Biotechnology Information at the World Wide Web at ncbi.nlm.nih.gov.

The following examples are intended to illustrate but not to limit the invention.

Example 1

Cloning and Construction

As exemplified herein, the target sequences (SEQ ID NO:1 and SEQ ID NO:2) were selected from a potato spindle tuber viroid (isolate 21008470, NCBI website, Accession Number AY372398) and a *Methanosarcina acetivorans* (M.a.I1-1) chloroplast-like type II intron (Accession Number AE011073) found on the World Wide Web at fp.ucalgary.ca/group2introns/species.htm), respectively. The full length potato spindle tuber viroid and chloroplast-like type II intron sequences were entered into PrimerExpress 2.0 (Applied Biosystems, Foster City, Calif.) to select primer/probe sets for use with the Applied Biosystems real-time quantitative PCR TaqMan® assay.

The goal was to identify a relatively short sequence (encompassing a primer/probe set) from each full length sequence that could be subcloned to engineer and construct calibrator polynucleotides. Once selected, sequences 5' and 3' to the region encompassing the selected primer/probe set were excluded. The selected regions were also shortened to be less than about 100 bases by excluding sequences that lay within the primer/probe set region, but outside the sequences where the primers and probes would anneal.

For the potato spindle tuber viroid sequence, the following sequence was selected (forward and reverse Q-PCR primers are underlined, intervening polynucleotides are in regular font, and the target sequence is in bold):

(SEQ ID NO: 3)
5' GGAGTAATTCCCGCCGAAACAGGGTTTTCCTGTCGCTTCGGCTAC TACCCGGTGGAAACAACTGAAGCTCCCGAGAACCG 3'

For the chloroplast-like type II intron sequence, the following sequence was selected (forward and reverse qPCR primers are underlined and the target sequence is in bold):

(SEQ ID NO: 4)
5' GAACTCCCGGAATTGATGGAATTATCTGGTAGATGCGTTCCGCTT TACAACTAACGAACAAGGGCTACAAGTACATTCGAAAGAAGAACGGTA AA 3'

Single-stranded oligonucleotides of these sequences were purchased from Invitrogen (Carlsbad, Calif.) and used as template in PCR to amplify and clone the sequences.

The forward and reverse primers used to amplify SEQ ID NO:3 for cloning were:

(SEQ ID NO: 9)
5' CGTAGCGGTACCGGAGTAATTCCCGCCGAAACA 3'
(Kpn I site underlined);
and (SEQ ID NO: 10)
5' CGCCGGGTCGACCGGTTCTCGGGAGCTTCAGTT 3'
(Sal I site underlined), respectively.

The forward and reverse primers used to amplify SEQ ID NO:4 for cloning were:

(SEQ ID NO: 11)
5' CGTAGCGGTACCGAACTCCCGGAATTGATGGAAT 3'
(Kpn I site underlined)
and (SEQ ID NO: 12)
5' CGCCGGGTCGACTTTACCGTTCTTCTTTCGAATGTACTTG 3'
(Sal I site underlined), respectively.

As shown in FIG. 1A, the resulting PCR products were digested with Kpn I and Sal I. The products were cloned (in separate reactions) into the Kpn I and Sal I sites of the pTNT vector (Promega, Madison, Wis.) and confirmed by sequencing.

Example 2

Generating Template for In vitro Production of Calibrator Polynucleotide

A certain amount of transcript runoff past the T7 transcription terminator was observed when using circular plasmid as template in a T7 RNA polymerase-driven in vitro transcription reaction. Linearizing the plasmid eliminates the problem of transcription runoffs; however, the best results were obtained by amplifying the functional transcription region of the plasmid (T7 promoter, insert, poly A, and T7 terminator) by PCR, and then using this PCR product as template in an in vitro transcription reaction.

Figure 1B:
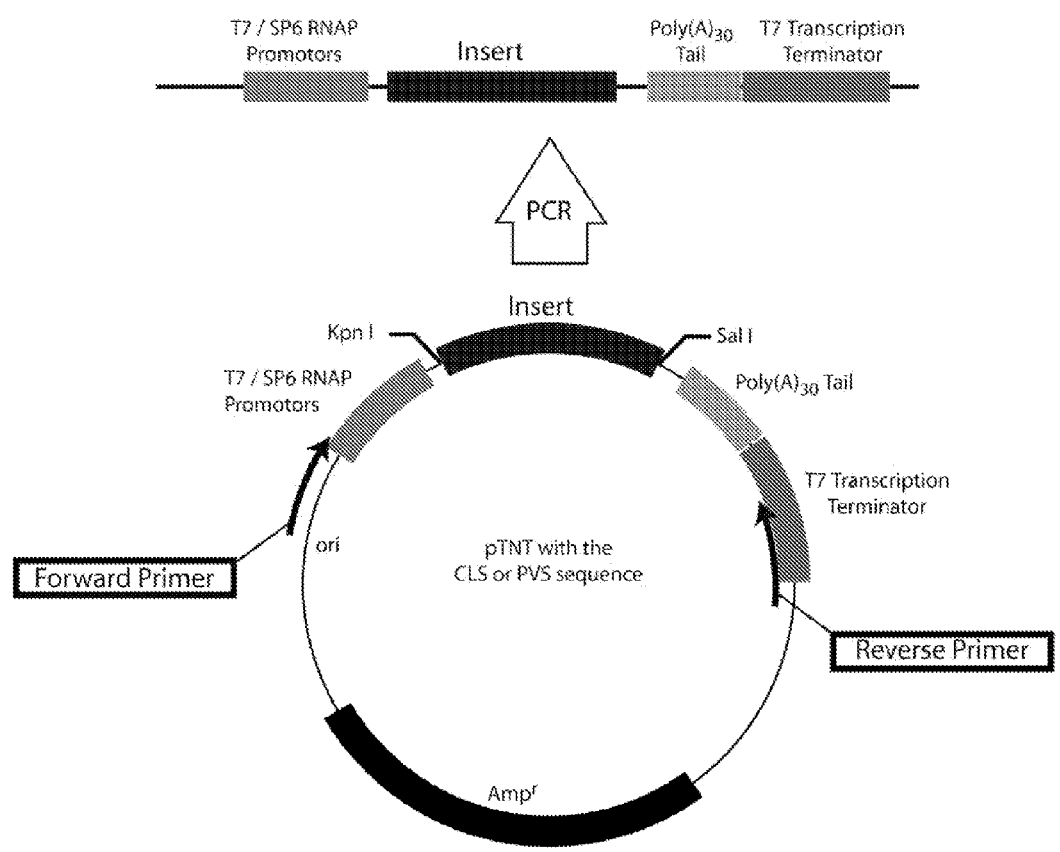
FIG. 1B shows the resulting product that was used as template in in vitro transcription reactions to generate the calibrator polynucleotide RNA.
Figure 2:
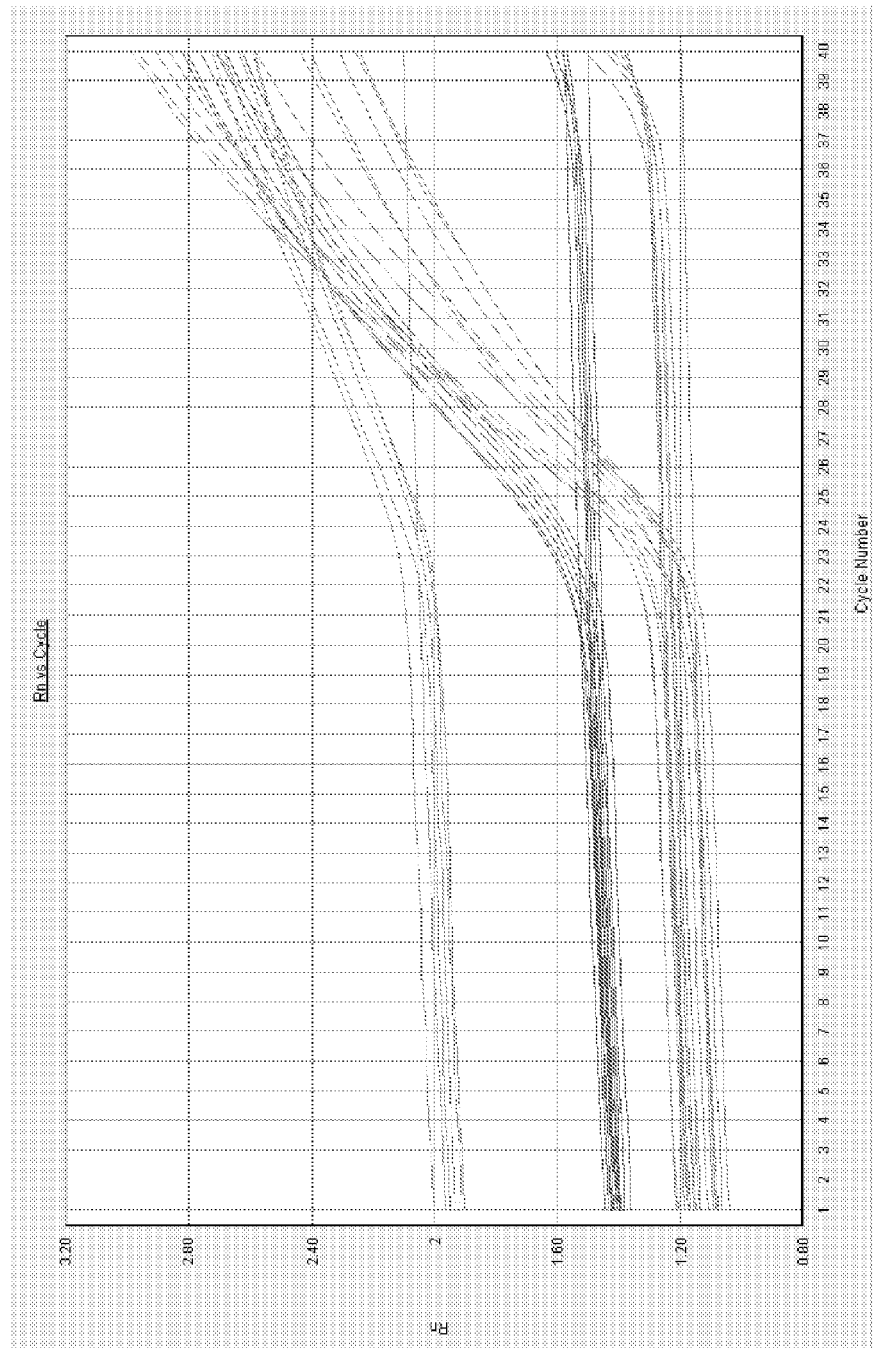
FIG. 2 shows the amplification and detection of the target polynucleotides and human β-actin in a multiplexed Taqman sequence detection assay. 5 ng of human control total RNA extracted from HaCaT cells (a transformed human epidermal keratinocyte cell line) was utilized to test the multiplexed amplification and detection of human β-actin (bottom set of lines) in the presence of either the SEQ ID NO:1 (middle set of lines) or SEQ ID NO:2 (top set of lines). Half of the β-actin samples were multiplexed with SEQ ID NO:1 and half of the β-actin samples were multiplexed with SEQ ID NO:2. The amplification kinetics of SEQ ID NO:1 better match the amplification kinetics of β-actin compared to SEQ ID NO:2 in this particular situation.

This region was amplified by PCR using the forward primer 5' TAAGGCTAGAGTACTTAA 3' (SEQ ID NO:13) (anneals to nucleotides 1-18 on the parent plasmid (pTNT from Promega, GenBank accession #AF479322)) and the reverse primer was 5' GGATCCAAAAAACCCCTC 3' (SEQ ID NO:14) (anneals to nucleotides 195-213 on the parent plasmid (pTNT from Promega, GenBank accession #AF479322)). The T7 RNA polymerase promoter is positioned at nucleotides 16-34 on the parent plasmid (pTNT from Promega, GenBank accession #AF479322) and the transcription terminator is positioned at nucleotides 161-208 on the parent plasmid (pTNT from Promega, GenBank accession #AF479322). The resulting PCR product schematically shown in FIG. 1B was resolved on a 1.5% agarose gel, extracted with a gel extraction kit (Qiagen, Valencia, Calif.), and quantified by spectrophotometry using methods known in the art.

Example 3

Quantitative Real-Time PCR

All quantitative real-time PCR (Q-PCR) was performed with Taq-Man® PCR reagents and analyzed using the ABI 7500 Sequence Detection System (Applied Biosystems, Foster City, Calif.). The primers and probes for each target sequence were individually optimized for maximum amplification efficiency using methods known in the art. A validation experiment was performed to demonstrate that each polynucleotide of interest and endogenous target sequence in a multiplex reaction maintained equal efficiencies.

Total RNA from HaCaT cells was purified using an RNeasy® Kit (Qiagen, Valencia, Calif.) and DNAse-I-treated on a purification column according to the manufacturer's protocol (Qiagen, Valencia, Calif.). The reverse transcription reaction was carried out using about 1 µg of total RNA (final concentration about 50 ng/µl) using SuperScript II reverse transcriptase (Invitrogen, Carlsbad, Calif.). After completion of cDNA synthesis, all reactions were diluted to a final RNA input concentration of about 5 ng/µl. For each gene analyzed, the experimental samples being tested were run in triplicate (three technical replicates) along with the corresponding no-template control and no-amplification control. The primer and probe pair concentrations used for each target sequence are as follows: β-actin=300 nM forward primer, 300 nM reverse primer, 250 nM FAM (6-carboxyfluoresein, a single isomer derivative of fluorescein) labeled probe; SEQ ID NO:3=300 nM forward primer, 300 nM reverse primer, 250 nM VIC (a fluorescent molecule) labeled probe; SEQ ID NO:4=300 nM forward primer, 300 nM reverse primer, 250 nM VIC labeled probe. Amplification reactions were carried out using the instrument default cycle conditions as follows: Stage 1 at 50° C. for 2 minutes; Stage 2 at 95° C. for 10 minutes; Stage 3 at 95° C. for 15 seconds followed by 60° C. for 1 minute. Stage three is repeated for a total of 40 cycles.

Example 4

Comparison of Q-PCR Assays Using Calibrator Polynucleotides

The effects of the toxic industrial chemical carbonyl chloride (phosgene) on rodent lung tissue were previously conducted using Q-PCR assays on selected genes of interest. See Sciuto et al. (2005) Genomic analysis of murine pulmonary tissue lung following carbonyl chloride inhalation. Chem. Res. Tox. 18(11):1654-1660, which is herein incorporated by reference. To confirm the Q-PCR assays and validate the calibrator polynucleotides for normalization and exemplify the improved accuracy of using calibrator polynucleotides as compared to the commonly used housekeeping gene, the following may be conducted:

I. Exogenously Added Calibrator Polynucleotide

Frozen total RNA previously isolated from the lungs of control and phosgene-exposed mice according to Sciuto et al. (2005) is thawed on ice. An empirically determined amount of calibrator polynucleotide is introduced into each sample, such that the ratio of a calibrator polynucleotide according to the present invention to endogenous mRNA does not exceed the amplification limits of the total RNA sample for purposes of multiplex Q-PCR.

II. cDNA Synthesis and Q-PCR

Reverse transcription is carried out using about 1 µg of total RNA in a final reaction concentration of about 50 ng/µl using Superscript II reverse transcriptase, dithiothreitol (DTT), poly dT oligonucleotide primer, dNTP and first strand buffer at about 42° C. for about 2 hours. After completion of cDNA synthesis, all reactions are diluted to a final RNA input concentration of about 5 ng/µl. All Q-PCR are performed using Taq-Man® PCR reagents and analyzed using the ABI 7500 Sequence Detection System (Applied Biosystems, Foster City, Calif.). Target primers and probes used for Q-PCR are designed using ABI Prism Primer Express V2.0 (Applied Biosystems, Foster City, Calif.). All primer and probe sets used to analyze specific genes altered by phosgene exposure (e.g. superoxide dismutase 3; see Sciuto et al. (2005) for complete list) are optimized using methods known in the art for appropriate primer and probe concentrations to maximize amplification efficiency with the added calibrator polynucleotide. All PCR reactions are performed using default thermocycler conditions which are as follows. Stage 1 at about 50° C. for about 2 minutes, stage 2 at about 95° C. for about 10 minutes, stage 3 at about 95° C. for about 15 seconds followed by about 60° C. for about 1 minute. Stage three is repeated for a total of about 40 cycles.

III. Q-PCR Expression Analysis

All cycle threshold values (Ct) collected by the ABI 7500 Sequence Detection System are exported into an Excel spreadsheet (Microsoft) where the absolute value of the difference between target gene Ct value and calibrator polynucleotide Ct value are calculated to normalize each sample and are referred to as the ΔCt. To determine changes in expression levels between exposed and control samples the ΔCt control are subtracted from the ΔCt of the exposed to obtain the ΔΔCt value and expressed graphically as $2^{-\Delta\Delta Ct}$.

By comparing the results of these experiments with the previously published data (Sciuto et al. (2005)) it is expected that the fluctuation of standard housekeeping genes will be observable and that the potential inaccuracy of using internal control housekeeping genes will be demonstrated under various experimental conditions as compared to the calibrator polynucleotides of the present invention.

Example 5

Q-PCR Assay and Sulfur Mustard

Various Q-PCR assays of selected nucleic acid molecules from tissue exposed to alkylating agents, such as the potent alkylating agent sulfur mustard, may be conducted using the calibrator polynucleotide for normalization. Previously, it has been shown that prior art housekeeping genes are not suitable for accurate normalization and determination of expression levels genes exposed to sulfur mustard exposures. See Dillman et al. (2005) Genomic Analysis of Rodent Pulmonary Tissue Following Bis(2-Chloroethyl) Sulfide Exposure. Chem. Res. Toxicol. 18:28-34, which is herein incorporated by reference. Thus, to show the that the calibrator polynucleotides of the present invention may be successfully used in situations where prior art housekeeping genes are not stably expressed, the following blind experiment, wherein the person performing the Q-PCR assay is blinded to the gene being analyzed and blinded to treatment conditions of the samples:

I. Exogenously Added Calibrator Polynucleotide

Frozen total RNA previously isolated from the lungs of control and sulfur mustard-exposed rats using methods known in the art are thawed on ice. An empirically determined amount of a calibrator polynucleotide is introduced into each sample, such that the ratio of calibrator polynucleotide to endogenous mRNA does not exceed the amplification limits of the total RNA sample for purposes of multiplex Q-PCR using methods known in the art.

II. cDNA Synthesis and Q-PCR

Reverse transcription is carried out using about 1 µg of total RNA in a final reaction concentration of about 50 ng/µl using Superscript II reverse transcriptase, dithiothreitol (DTT), poly dT oligonucleotide primer, dNTP and first strand buffer at about 42° C. for about 2 hours using methods known in the art. After completion of cDNA synthesis, all reactions are diluted to a final RNA input concentration of about 5 ng/µl using methods known in the art. All Q-PCR are performed using Taq-Man® PCR reagents and analyzed using the ABI 7500 Sequence Detection System (Applied Biosystems, Foster City, Calif.) using methods known in the art. Target primers and probes used for Q-PCR are designed using ABI Prism Primer Express V2.0 (Applied Biosystems, Foster City, Calif.) using methods known in the art. All primer and probe sets used to analyze specific housekeeping genes are optimized, using methods known in the art, for appropriate primer and probe concentrations to maximize amplification efficiency with the added calibrator polynucleotide. All PCR reactions are performed using default thermocycler conditions which are as follows. Stage 1 at about 50° C. for about 2 minutes, stage 2 at about 95° C. for about 10 minutes, stage 3 at about 95° C. for about 15 seconds followed by about 60° C. for about 1 minute. Stage three is repeated for a total of about 40 cycles.

III. Q-PCR Expression Analysis

All cycle threshold values (Ct) collected by the ABI 7500 Sequence Detection System are exported into a spreadsheet where the absolute value of the difference between target gene Ct value and calibrator polynucleotide Ct value are calculated to normalize each sample and are referred to as the $\Delta$Ct. To determine changes in expression levels between exposed and control samples the $\Delta$Ct control are subtracted from the $\Delta$Ct of the exposed to obtain the $\Delta\Delta$Ct value and expressed graphically using $2^{-\Delta\Delta Ct}$.

By comparing the results of these experiments with the previously published data (Dillman et al., 2005) it is expected that the fluctuation of standard housekeeping genes will be observable and that the potential inaccuracy of using internal control housekeeping genes will be demonstrated under various experimental conditions as compared to the calibrator polynucleotides of the present invention.

Example 6

Comparison of Housekeeping Genes and Calibrator Polynucleotides

Figure 3:
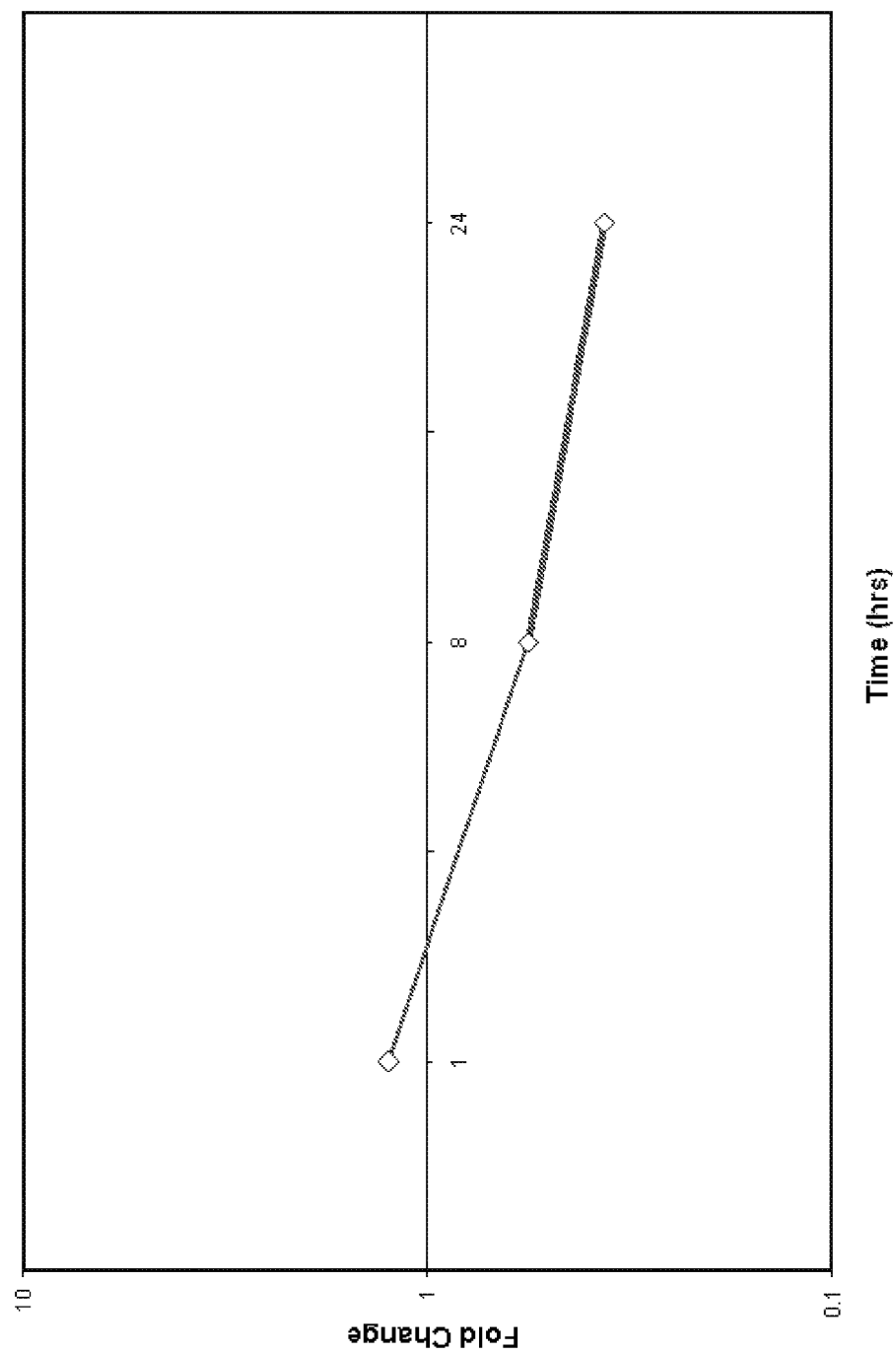
FIG. 3 shows the relative quantification of human β-actin transcripts in sulfur mustard-exposed HaCaT cells using the PVS calibrator polynucleotide for normalization. 5 pg of SEQ ID NO:1 was spiked into 5 ng of RNA isolated from control HaCaT cells or into 5 ng of RNA isolated from HaCaT cells exposed to 200 µM sulfur mustard. β-actin transcript levels were measured and normalized to the exogenous target sequence having SEQ ID NO:1 for all samples. The unexposed control samples were compared to the sulfur mustard-exposed samples for the time points of 1 hour, 8 hours, and 24 hours to estimate fold-change differences. These results reveal that β-actin levels decrease following exposure to sulfur mustard and suggest that β-actin is not an appropriate internal standard to measure gene expression levels in sulfur mustard-exposed cells or tissues.

The improved performance and increased accuracy of the calibrator polynucleotides of the present invention over prior art housekeeping genes (e.g. beta-actin, GAPDH, tubulin, etc.) may be shown according to the following (as exemplified in FIG. 3):

I. In Vitro Human Epidermal Keratinocyte Exposure

Human epidermal keratinocytes (Cascade Biologics, Portland, Oreg.) seeded at a density of about $2.5 \times 10^3$ cells/cm$^2$ at about 80% confluency is exposed to about 25 µM or about 400 µM bis(2-chlorethyl)sulfide (sulfur mustard), or cell culture media (EpiLife, Cascade Biologics) alone as a control at about 37° C. using methods known in the art. Cells lysates are collected, using methods known in the art, at about 1 hour, about 2 hours, about 8 hours, and about 16 hours post-exposure for analysis.

II. Cell Collection

Once the appropriate time point is reached for each exposed and control sample, cells are removed from about 37° C. incubation and media is aspirated followed by two 10 ml washes with Hank's balanced salt solution (Sigma-Aldrich, St. Louis, Mo.) using methods known in the art. The cells are trypsinized with about 4 ml of trypsin (about 0.025% w/v) for about 6 to about 8 minutes, neutralized using about 4 ml of trypsin neutralization buffer, collected, dispensed into a 50 ml polypropylene tube and pelleted by centrifugation at about 180×g for about 10 minutes using methods known in the art. The supernatant is removed and the cell pellet is resuspended in about 2 ml of cell culture media using methods known in the art. Cell concentration is determined with a hemocytometer using methods known in the art. About $5 \times 10^5$ cells is dispensed into a 1.5 ml microfuge tube for each sample and centrifuged at about 180×g for about 10 minutes using methods known in the art. The supernatant is removed and about 375 µl of buffer RLT (RNEasy lysis buffer, Qiagen, Valencia, Calif.) is applied to the pellet for total cellular lysis using methods known in the art. Samples are stored at about –80° C. prior to quantitative PCR (Q-PCR) analysis.

III. Experimental Design

Several prior art housekeeping genes may be compared to the calibrator polynucleotide for normalization in Q-PCR. A representative list of prior art housekeeping genes (See e.g. Eisenberg & Levanon (2003) Human housekeeping genes are compact. Trends in Genetics. 19:362-365, which is herein incorporated by reference) for Q-PCR is given below:

NM001101 actin, beta (ACTB)
NM000034 aldolase A, fructose-bisphosphate (ALDOA)
NM002046 glyceraldehyde-3-phosphate dehydrogenase (GAPD)

NM000291 phosphoglycerate kinase 1 (PGK1)
NM005566 lactate dehydrogenase A (LDHA)
NM002954 ribosomal protein S27a (RPS27A)
NM000981 ribosomal protein L19 (RPL19)
NM000975 ribosomal protein L11 (RPL11)
NM007363 non-POU domain containing, octamer-binding (NONO)
NM004309 Rho GDP dissociation inhibitor (GDI) alpha (ARHGDIA)
NM000994 ribosomal protein L32 (RPL32)
NM022551 ribosomal protein S18 (RPS18)
NM007355 heat shock 90kDa protein 1, beta (HSPCB)

Frozen RLT lysates are thawed on ice prior to isolation of total RNA using methods known in the art. An empirically determined amount of calibrator polynucleotide is introduced into each sample, such that the ratio of calibrator polynucleotide to endogenous mRNA does not exceed the amplification limits of the total RNA sample for purposes of multiplex Q-PCR using methods known in the art.

IV. RNA Extraction and Purification

Frozen RLT lysates are thawed on ice and total RNA is extracted using RNAeasy minicolumn total RNA isolation kits (Qiagen, Valencia, Calif.) according to the manufacturer's protocol. Briefly, RNA is precipitated with ethanol then bound to the RNAeasy minicolumn. Each sample is then washed once with buffer RW1 and then treated with RNase-free DNAse I for on-column DNAse digestion to remove genomic DNA. The columns are then washed two additional times with buffer RPE and total RNA is eluted with about 60 μl of RNase-free water. Samples are then analyzed using a NanoDrop ND-1000 UV-Vis Spectrophotometer (Nanodrop Technologies, Rockland, Del.) to determine sample concentration and quality using methods known in the art. Samples are further analyzed using an Agilent Bioanalyzer (Agilent, Palo Alto, Calif.) to determine RNA integrity using methods known in the art.

V. cDNA Synthesis and Q-PCR

The reverse transcription reaction is carried out using about 1 μg of total RNA in a final reaction concentration of about 50 ng/μl using Superscript II reverse transcriptase, dithiothreitol (DTT), poly dT oligonucleotide primer, dNTP and first strand buffer at about 42° C. for about 2 hours using methods known in the art. After completion of cDNA synthesis, all reactions are diluted to a final RNA input concentration of about 5 ng/μl using methods known in the art. All Q-PCR are performed using Taq-Man® PCR reagents and analyzed using the ABI 7500 Sequence Detection System (Applied Biosystems, Foster City, Calif.) using methods known in the art. Target primers and probes used for Q-PCR are designed using ABI Prism Primer Express V2.0 (Applied Biosystems) using methods known in the art. All primer and probe sets used to analyze specific housekeeping genes are optimized, using methods known in the art, for appropriate primer and probe concentrations to maximize amplification efficiency with the added calibrator polynucleotide. All PCR reactions are performed using default thermocycler conditions which are as follows. Stage 1 at about 50° C. for about 2 minutes, stage 2 at about 95° C. for about 10 minutes, stage 3 at about 95° C. for about 15 seconds followed by about 60° C. for about 1 minute. Stage three is repeated for a total of about 40 cycles.

VI. Q-PCR Expression Analysis

All cycle threshold values (Ct) collected by the ABI 7500 Sequence Detection System are exported into a spreadsheet where the absolute value of the difference between target gene Ct value and calibrator polynucleotide Ct value is calculated to normalize each sample and is referred to as the ΔCt.

To determine changes in expression levels between exposed and control samples the ΔCt control is subtracted from the ΔCt of the exposed to obtain the ΔΔCt value and expressed graphically as $2^{-\Delta\Delta Ct}$.

These experiments are expected to show the fluctuation of standard housekeeping genes and demonstrate the potential inaccuracy of using internal control housekeeping genes under various experimental conditions.

Example 7

Evaluation of Q-PCR Reproducibility Using Calibrator Polynucleotides

To show improved reproducibility of Q-PCR assays using the calibrator polynucleotides according to the present invention over those using prior art housekeeping genes, the following may be conducted. A calibrator polynucleotide according to the present invention is added to a test sample that is then divided into equal parts and each part is analyzed by a different technician.

I. In Vitro Human Epidermal Keratinocyte Exposure

Human epidermal keratinocytes (Cascade Biologics, Portland, Oreg.) seeded at a density of about $2.5 \times 10^3$ cells/cm² at about 80% confluency is exposed to about 25 μM or about 400 μM bis(2-chloroethyl)sulfide (sulfur mustard), or cell culture media (EpiLife, Cascade Biologics) alone as a control at about 37° C. using methods known in the art. Cell lysates are collected at about 1 hour, about 2 hours, about 8 hours, and about 16 hours post-exposure for analysis using methods known in the art.

II. Cell Collection

Once the appropriate time point is reached for each exposed and control sample, cells are removed from about 37° C. incubation and media is aspirated followed by two 10 ml washes with Hank's balanced salt solution (Sigma-Aldrich, St. Louis, Mo.) using methods known in the art. The cells are trypsinized with about 4 ml of trypsin (0.025% w/v) for about 6 to about 8 minutes, neutralized using about 4 ml of trypsin neutralization buffer, collected, dispensed into a 50 ml polypropylene tube and pelleted by centrifugation at about 180×g for about 10 minutes using methods known in the art. The supernatant is removed and the cell pellet is resuspended in about 2 ml of cell culture media using methods known in the art. Cell concentration is determined with a hemocytometer using methods known in the art. About $5 \times 10^5$ cells is dispensed into a 1.5 ml microfuge tube for each sample and centrifuged at about 180×g for about 10 minutes using methods known in the art. The supernatant is removed and about 375 μl of buffer RLT (RNEasy lysis buffer, Qiagen, Valencia, Calif.) is applied to the pellet for total cellular lysis using methods known in the art. Samples are frozen at about −80° C. prior to quantitative PCR (Q-PCR) analysis.

III. Exogenously Added Calibrator Polynucleotide

Frozen RLT lysate is thawed on ice prior to isolation of total RNA using methods known in the art. The test samples will each be divided into two equal parts. An empirically determined amount of calibrator polynucleotide is introduced into one part by a single technician, such that the ratio of calibrator polynucleotide to endogenous mRNA does not exceed the amplification limits of the total RNA sample for purposes of multiplex Q-PCR. The other part will not receive calibrator polynucleotide. The samples will then be divided equally among three different technicians. Each of the technicians will then carry out the methods described below on the two different parts of each sample. In the part with the calibrator polynucleotide introduced, the calibrator polynucleotide is used to normalize across the equivalent calibrator polynucleotide-containing parts. The other part will not have calibrator polynucleotide introduced, but instead an endogenous housekeeping gene (e.g. beta actin) is used for normalization.

IV. RNA Extraction and Purification

Frozen RLT lysates are thawed on ice and total RNA are extracted using
RNAeasy minicolumn total RNA isolation kits (Qiagen, Valencia, Calif.) according to the manufacturer's protocol. Briefly, RNA is precipitated with ethanol then bound to the RNAeasy minicolumn. Each sample is then washed once with buffer RW1 and then treated with RNase-free DNase I for on-column DNase digestion to remove genomic DNA. The columns are then washed two additional times with buffer RPE and total RNA is eluted with about 60 µl of RNase-free water. Samples are then analyzed using a Nano-Drop ND-1000 UV-Vis Spectrophotometer (Nanodrop Technologies, Rockland, Del.) to determine sample concentration and quality using methods known in the art. Samples are further analyzed using an Agilent Bioanalyzer (Agilent, Palo Alto, Calif.) to determine RNA integrity using methods known in the art.

V. cDNA Synthesis and Q-PCR

The reverse transcription reaction is carried out using about 1 µg of total RNA in a final reaction concentration of about 50 ng/µl using Superscript II reverse transcriptase, dithiothreitol (DTT), poly dT oligonucleotide primer, dNTP and first strand buffer at about 42° C. for about 2 hours using methods known in the art. After completion of cDNA synthesis, all reactions are diluted to a final RNA input concentration of about 5 ng/µl using methods known in the art. All Q-PCR are performed using Taq-Man® PCR reagents and analyzed using the ABI 7500 Sequence Detection System (Applied Biosystems, Foster City, Calif.) using methods known in the art. Target primers and probes used for Q-PCR are designed using ABI Prism Primer Express V2.0 (Applied Biosystems). All primer and probe sets used to analyze specific target genes are optimized, using methods known in the art, for appropriate primer and probe concentrations to maximize amplification efficiency with the added calibrator polynucleotide or the housekeeping gene (e.g. beta-actin). All PCR reactions are performed using default thermocycler conditions which are as follows. Stage 1 at about 50° C. for about 2 minutes, stage 2 at about 95° C. for about 10 minutes, stage 3 at about 95° C. for about 15 seconds followed by about 60° C. for about 1 minute. Stage three is repeated for a total of about 40 cycles.

VI. Q-PCR Expression Analysis

All cycle threshold values (Ct) collected by the ABI 7500 Sequence Detection System are exported into a spreadsheet where the absolute value of the difference between target gene Ct value and calibrator polynucleotide Ct value or the housekeeping gene (e.g. beta actin) Ct value is calculated to normalize each sample and is referred to as the ΔCt. To determine changes in expression levels between exposed and control samples the ΔCt control is subtracted from the ΔCt of the exposed to obtain the ΔΔCt value and expressed graphically as $2^{-\Delta\Delta Ct}$. The results from each of the three technicians are compared relative to one another. The samples containing the calibrator polynucleotide are compared using the calibrator polynucleotide for normalization.

These experiments are expected to show that variations (or error) in assay results due to the inherent variability introduced by different technicians performing the same technique are eliminated by using the levels of the calibrator polynucleotides to normalize across samples. Consequently, a calibrator polynucleotide according to the present invention may be added to a sample prior to analysis to increase precision and reproducibility. Thus, the present invention provides assay kits packaged together with at least one calibrator polynucleotide according to the present invention.

Example 8

Comparison of Housekeeping Genes and Calibrator Polynucleotides in Human Clinical Samples The calibrator polynucleotides of the present invention may be used in assays for assaying the expression level of a marker (e.g. cytokeratin 17 (CK17) in oral or oropharyngeal squamous cell carcinoma for a given disease or disorder in a human or animal. See Garrel R, Dromard M, Costes V, Barbotte E, Comte F, Gardiner Q, Cartier C, Makeieff M, Crampette L, Guerrier B, Boulle N. The diagnostic accuracy of reverse transcription-PCR quantification of cytokeratin mRNA in the detection of sentinel lymph node invasion in oral and oropharyngeal squamous cell carcinoma: a comparison with immunohistochemistry. Clin Cancer Res. 2006 Apr. 15; 12(8):2498-505, which is herein incorporated by reference. For example, the following may be conducted:

I. Human Clinical Samples

Lymph node tissue from patients with squamous cell carcinoma of the head and neck is collected from clinical collaborators. Frozen tissue is homogenized in Tri Reagent (Sigma-Aldrich Chemical Co., St. Louis, Mo.), and the total RNA is extracted according to the manufacturer's protocol (see the World Wide Web at sigmaaldrich.com/sigma/bulletin/t9424bul.pdf). RNA is purified using RNeasy columns (Qiagen, Valencia, Calif.) using methods known in the art.

II. Exogenously Added Calibrator Polynucleotide

Frozen lysates are thawed on ice prior to isolation of total RNA and divided into two sample sets using methods known in the art. An empirically determined amount of calibrator polynucleotide is introduced into one sample set, such that the ratio of calibrator polynucleotide to endogenous mRNA does not exceed the amplification limits of the total RNA sample for purposes of multiplex Q-PCR using methods known in the art. The other sample set will not receive calibrator polynucleotide and a housekeeping gene (e.g. beta actin) is used for normalization.

III. RNA Extraction and Purification

Frozen RLT lysate is thawed on ice and total RNA is extracted using RNeasy minicolumn total RNA isolation kits (Qiagen, Valencia, Calif.) according to the manufacturer's protocol. Briefly, RNA is precipitated with ethanol then bound to the RNeasy minicolumn. Each sample is then washed once with buffer RW1 and then treated with RNase-free DNase I for on-column DNase digestion to remove genomic DNA. The columns are then washed two additional times with buffer RPE and total RNA is eluted with about 60 µl of RNase-free water. Samples are then analyzed using a NanoDrop ND-1000 UV-Vis Spectrophotometer (Nanodrop Technologies, Rockland, Del.) to determine sample concentration and quality using methods known in the art. Samples are further analyzed using an Agilent Bioanalyzer (Agilent, Palo Alto, Calif.) to determine RNA integrity using methods known in the art.

V. cDNA Synthesis and Q-PCR

The reverse transcription reaction is carried out using about 1 µg of total RNA in a final reaction concentration of about 50 ng/µl using Superscript II reverse transcriptase, dithiothreitol (DTT), poly dT oligonucleotide primer, dNTP and first strand buffer at about 42° C. for about 2 hours using methods known in the art. After completion of cDNA synthesis, all reactions are diluted to a final RNA input concentration of about 5 ng/µl using methods known in the art. All Q-PCR is performed using Taq-Man® PCR reagents and analyzed using the ABI 7500 Sequence Detection System (Applied Biosystems, Foster City, Calif.) using methods known in the art. Target primers and probes used for Q-PCR are designed using ABI Prism Primer Express V2.0 (Applied Biosystems) using methods known in the art. All primer and probe sets used to analyze cytokeratin 17 are optimized, using methods known in the art, for appropriate primer and probe concentrations to maximize amplification efficiency with the added calibrator polynucleotide or housekeeping gene (beta actin). All PCR reactions are performed using default thermocycler conditions which are as follows. Stage 1 at about 50° C. for about 2 minutes, stage 2 at about 95° C. for about 10 minutes, stage 3 at about 95° C. for about 15 seconds followed by about 60° C. for about 1 minute. Stage three is repeated for a total of about 40 cycles.

VI. Q-PCR Expression Analysis

All cycle threshold values (Ct) collected by the ABI 7500 Sequence Detection System are exported into a spreadsheet where the absolute value of the difference between target gene (cytokeratin 17) Ct value and calibrator polynucleotide Ct value or housekeeping gene (e.g. beta actin) Ct value is calculated to normalize each sample and is referred to as the ΔCt. To determine changes in expression levels between exposed and control samples the ΔCt control is subtracted from the ΔCt of the exposed to obtain the ΔΔCt value and expressed graphically using $2^{-\Delta\Delta Ct}$.

These experiments are expected to show that use of the calibrator polynucleotide in Q-PCR increases the accuracy of disease diagnosis compared to using a housekeeping gene in Q-PCR. Thus, the calibrator polynucleotides of the present invention may be used in assays to detect and measure markers for disorders and diseases in human and animals. The calibrator polynucleotides of the present invention may be used in methods for diagnosing a human or animal subject as being afflicted with or suffering from a given disease or disorder which is identifiable by an abnormal level of a given nucleic acid molecule. The calibrator polynucleotides of the present invention may be used in conjunction with treatment methods, e.g. to determine whether a given therapy is having an effect on modulating the level of a given nucleic acid molecule associated with a given disease or disorder and modifying the therapy accordingly.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A nucleic acid molecule comprising a sequence having 95-100% sequence identity to SEQ ID NO:3 or its complement thereof.

2. An isolated nucleic acid molecule consisting of a sequence having 95-100% sequence identity to
SEQ ID NO:3 or its complement thereof.

3. The isolated nucleic acid molecule of claim 2, wherein the nucleic acid molecule is
SEQ ID NO:3 or its complement thereof.

4. A kit comprising the nucleic acid molecule according to claim 1 packaged together with at least one reagent for conducting a nucleic acid hybridization assay.

5. A kit comprising the nucleic acid molecule according to claim 2 packaged together with at least one reagent for conducting a nucleic acid hybridization assay.

6. A kit comprising the nucleic acid molecule according to claim 3 packaged together with at least one reagent for conducting a nucleic acid hybridization assay.

* * * * *